(12) United States Patent (10) Patent No.: US 7,932,326 B2
Yokel et al. (45) Date of Patent: Apr. 26, 2011

(54) CHELATING COMPOUNDS AND IMMOBILIZED TETHERED CHELATORS

(75) Inventors: Robert A. Yokel, Lexington, KY (US); Wesley R. Harris, St. Louis, MO (US); Christopher D. Spilling, St. Louis, MO (US); Chang-Guo Zhan, Lexington, KY (US)

(73) Assignee: The University of Kentucky Research Foundation, Lexington, KY (US)

( * ) Notice: Subject to any disclaimer, the term of this patent is extended or adjusted under 35 U.S.C. 154(b) by 480 days.

(21) Appl. No.: 12/104,066

(22) Filed: Apr. 16, 2008

(65) Prior Publication Data

US 2009/0261043 A1 Oct. 22, 2009

(51) Int. Cl.
*B01D 15/38* (2006.01)
(52) U.S. Cl. ....... 525/333.6; 558/447; 560/12; 560/170; 562/621
(58) Field of Classification Search .................. 526/621; 525/333.6; 560/12, 170; 558/447
See application file for complete search history.

(56) References Cited

U.S. PATENT DOCUMENTS

| | | | |
|---|---|---|---|
| 4,599,361 A | 7/1986 | Dickens et al. |
| 4,654,299 A | 3/1987 | Lentfer |
| 4,666,927 A | 5/1987 | Hider et al. |
| 4,671,901 A | 6/1987 | Green |
| 4,684,482 A | 8/1987 | Green |
| 5,089,644 A | 2/1992 | Quay et al. |
| 5,104,865 A | 4/1992 | Hider et al. |
| 5,254,724 A | 10/1993 | Bergeron, Jr. |
| 5,312,730 A | 5/1994 | Piran et al. |
| 5,332,679 A | 7/1994 | Simons et al. |
| 5,424,219 A | 6/1995 | Jirikowski |
| 5,663,201 A | 9/1997 | Lowther et al. |
| 5,728,681 A | 3/1998 | Kido et al. |
| 5,739,167 A | 4/1998 | Lowther et al. |
| 5,756,825 A | 5/1998 | Safavy et al. |
| 6,022,865 A | 2/2000 | Deutsch |
| 6,071,412 A | 6/2000 | Ambrus et al. |
| 6,132,750 A | 10/2000 | Perrier et al. |
| 6,391,980 B1 | 5/2002 | Clark |
| 6,693,173 B2 | 2/2004 | Mamidi et al. |
| 6,858,414 B2 | 2/2005 | Keri et al. |
| 2005/0276862 A1 | 12/2005 | Bringley et al. |
| 2005/0277752 A1 | 12/2005 | Bringley et al. |
| 2006/0211773 A1* | 9/2006 | Bergeron .................. 514/697 |

FOREIGN PATENT DOCUMENTS

| | | |
|---|---|---|
| CN | 1413773 | 4/2003 |
| WO | WO 93/00327 | 1/1993 |

OTHER PUBLICATIONS

Liu, et al., Synthesis and Coordination Behaviour of Hydroxamate Resin with Varying Spacer Groups, Polyhedron vol. 11, No. 5, pp. 551-558, 1992, Great Britain.
Vernon, Frederick, Chelating Ion Exchangers—The Synthesis and Uses of Poly(hydroxamic Acid) Resins, Pure and Appl. Chem., vol. 54, No. 11, pp. 2151-2158, 1982, Great Britain.

(Continued)

*Primary Examiner* — Chester T Barry
(74) *Attorney, Agent, or Firm* — King & Schickli, PLLC

(57) ABSTRACT

Novel di- and tripodal compounds useful as chelators, intermediates for their production and a method for treating an aqueous solution to remove trivalent metal ions are presented.

8 Claims, 5 Drawing Sheets

OTHER PUBLICATIONS

Crumbliss, et al., Synthesis and Characterization of Iron(III) Chelating Analogues of Siderophores on Organic Solid Supports, Inorganica Chemica Acta, 133 (1987) 281-287, Switzerland.

Hutchinson, et al., Solid phase extraction of metal ions using immobilised chelating calixarene tetrahydroxamates, Analytica Chimica Acta 291 (1994 269-275, Elsevier Science B.V.

Lu, et al., Kinetic studies of aluminum and zinc speciation in river water and snow, Analytica Chimica Acta 293 (1994) 95-108, Elsevier Science B.V.

Philips et al., Extraction of Metal Ions by N-Phenyl-, N-Methyl-, and N-Unsubstituted Hydroxamic Acid Resins, Analytica Chimica Acta, 139 (1982) 237-249, Elsevier Scientific Publishing Company, Amsterdam.

Evers et al., Similarities Between Al(3) and Fe3, Evers et al. Inorg. Chem. 1989, 28: 2189.

MBA Tech Connection, Intellectual Property Overview Report, Aluminum Chelator Concept, undated, pp. 1-26.

Dr. Yokel, Reduction of Toxicity in the Premature Neonate Associated with Aluminum as a Contaminant of Total Parenteral Nutrition Solutions, Thrasher Research Fund Award, No. 02818-1. 2004, pp. 1-5.

Dr. Robert A. Yokel, Reduction of Toxicity in the Premature Neonate Associated with Aluminum as a Contaminant of Total Parenteral Nutrition Solutions. Thrasher Research Fund, Award No. 02818-1, Twelve Month Research Progress Report.

Dr. Robert A. Yokel, Reduction of Toxicity in the Premature Neonate Associated with Aluminum as a Contaminant of Total Parenteral Nutrition Solutions. Thrasher Research Fund. Award No. 02818-1. Eighteen Month Research Progress Report (undated), pp. 1-4.

Dr. Robert A. Yokel, Semiannual Progress Report. Thrasher Research Fund, Feb. 14, 2006, Reporting Period Mar. 1, 2005 to Aug. 31, 2005. Award No. 02818-1. pp. 1-4.

Dr. Robert A. Yokel, Reduction of Toxicity in the Premature Neonate Associated with Aluminum as a Contaminant of Total Perenteral Nutrition Solutions. Thrasher Research Project. Scientific Abstract; Award 02818.1. (undated); pp. 4-17.

Chen & Zhan, Computational Modeling of Aluminum (III)-Ligand Binding. University of Kentucky; Jan. 18, 2006; pp. 1-3.

Dr. Robert A. Yokel et al. Reduction of Toxicity in the Premature Neonate Associated with Aluminum as a Contaminant of Total Parenteral Nutrition Solutions. Pharmacy College, University of Kentucky. (undated).

* cited by examiner

CHELATING COMPOUNDS AND IMMOBILIZED TETHERED CHELATORS

TECHNICAL FIELD AND INDUSTRIAL APPLICABILITY OF THE INVENTION

The present invention relates generally to the chemical field and, more particularly, to novel chelating agents, useful intermediates for synthesizing those chelating agents, the immobilization of those agents on a solid support resin, and the use of those chelating resins to remove metal ions from aqueous solutions.

BACKGROUND OF THE INVENTION

A chelator or chelating agent is a polydentate ligand that bonds to more than one coordination site of a metal ion. Chelating agents have long been known in the art to be useful in chemical analysis, in environmental remediation and in medicine. In chelation therapy, a chelating agent is employed to bind a poisonous metal agent such as mercury, arsenic, iron, lead or aluminum in order to displace the ion from biological ligands such as proteins and convert the metal ion into a less toxic form that can be excreted without further interaction with the body.

The present invention relates to (1) novel chelating agents or compounds, (2) novel immobilized, tethered chelators comprising the novel chelating compounds linked to immobilized supports and (3) methods of employing the novel compounds and chelators to remove trivalent metals such as $Al^{3+}$ from aqueous systems in situ, in vivo and in vitro.

There have been previous studies of tripodal, trihydroxamic acids. Most of these ligands are based on tripodal platforms of tris(2-aminethyl)amine(tren) (Matsumoto et al., Chem. Commun. 2001, 978-979; Matsumoto et al., Inorg. Chem., 2001, 40: 190-191; Matsumoto et al., Inorg. Chem, 2004, 43: 8538-8546; Ng et al., Inorg. Chem. 1989, 28: 2062-2066), tris(3-aminopropyl)amine (Matsumoto et al., Eur. J. Inorg. Chem, 2001, 2481-2484); or nitrilotriacetic acid (nta) (Lee et al, J. Med. Chem. 1985, 28: 317-323; Hara et al., Inorg. Chem. 2000, 39: 5074-5082). These studies teach that such ligands form $Fe^{3+}$ complexes with binding constants in the range of $10^{28}$ to $10^{33}$, so long as there are five or six atoms connecting the bridgehead atom of the platform and the first atom of the hydroxamate functional group on the sidearm (Matsumoto et al., Eur. J. Inorg. Chem. 2001, 2481-2484; Matsumoto et al., Inorg. Chem. 2001, 40: 190-191; Ng et al., Inorg. Chem. 1989, 28: 2062-2066). These ligands include amide functional groups in the sidearms, and the iron complexes appear to be stabilized by intramolecular hydrogen bonding between the amide functional groups (Matsumoto et al., Inorg. Chem. 2001, 40:190-191).

The common feature of all the above ligands is that the bridgehead atom is a tertiary nitrogen. To attach these ligands to a solid support via this nitrogen would require the formation of a quaternary ammonium group. This is expected to have an adverse effect on the chelating ability of the ligand. It will introduce a permanent positive charge on the ligand, resulting in electrostatic repulsion of the target metal ion. In some cases, it will also require a change in the conformation of the metal complex.

A few tripodal tris(hydroxamate) ligands have been prepared in which the bridgehead atom is a carbon, rather than a nitrogen. These ligands are built on tripodal bases of either 1,1,1-tris(hydroxymethyl)ethane (Motekaitis et al., Inorg. Chem. 1991, 30: 1554-1556) or 1,1,1-tris(hydroxymethyl)propane (Dayan et al., Inorg. Chem. 1993, 32: 1467-1475). Hydroxamate groups were added to these tripodal bases through ether linkages. These studies teach that one needs 4 or 5 atoms between the bridgehead carbon and the first atom of the hydroxamate functional group for strong metal binding. The $Fe^{3+}$ complexes of these ligands have binding constants of $10^{26}$ to $10^{28}$. However, it is not possible to link these ligands to a polymeric support through the quaternary carbon bridgehead atom.

The current invention is based in the use of hydroxyalkylaminomethanes, especially the common buffer tris(1,1,1-tris(hydroxymethyl)aminomethane), as the tripodal base. The use of hydroxylalkylaminomethanes allows us to construct tripodal chelating functional groups that will mimic the high metal binding affinities of the ligands already in the literature, but it also provides a free amine group that can be used to easily attach the ligands to a variety of solid support.

SUMMARY OF THE INVENTION

In accordance with the purposes of the present invention as described herein, novel di- and tripodal compounds are disclosed for use as chelating agents. Such compounds include, but are not limited to, novel tripodal trihydroxamate chelating agents having a tris(hydroxylalky)aminomethane platform, such chelating agents bonded to a polymeric resin, useful intermediates for making such chelating agents and to a method of removing aluminum from a solution using such chelating agents.

In the following description there is shown and described several different embodiments of the invention, simply by way of illustration of some of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings, incorporated herein and forming a part of the specification, illustrate several aspects of the present invention and together with the description serve to explain certain principles of the invention. In the drawings.

DETAILED DESCRIPTION OF THE PREFERRED EMBODIMENTS OF THE INVENTION

Figure 1:
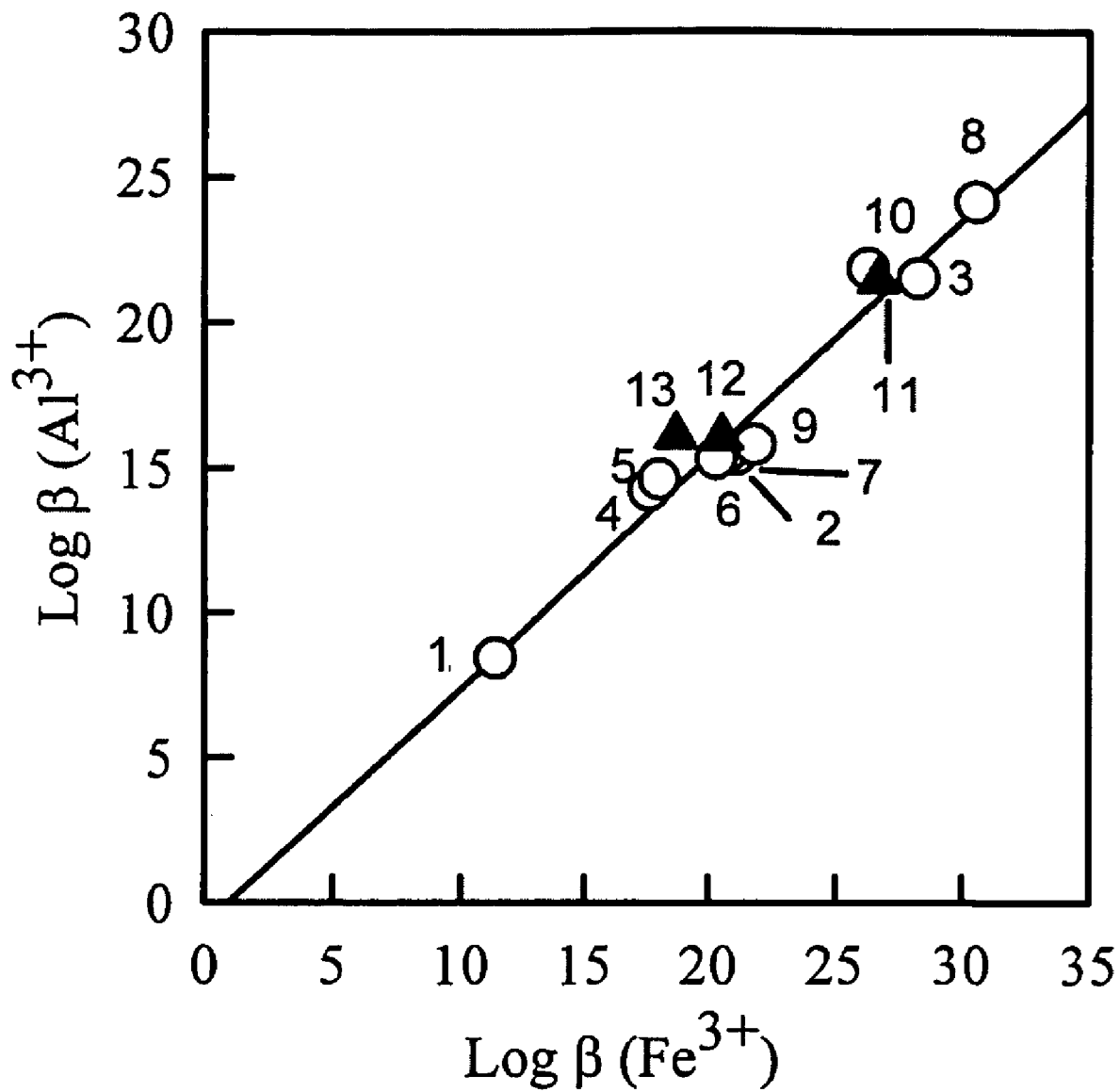
FIG. 1 is a linear free energy relationship showing the correlation between the binding affinities of $Fe^{3+}$ and $Al^{3+}$ with hydroxamate ligands. Each data point represents a ligand, with the log β value for $Fe^{3+}$ as the x-coordinate and the log β value for $Al^{3+}$ as the y-coordinate. The open symbols represent reference compounds described in the literature. The data points are: 1-3 represent the 1:1, 1:2, and 1:3 complexes with acetohydroxamic acid. Points 4-7 represent a series of linear dihydroxamates, in which the hydroxamate groups are separated by 4, 5, 6, or 7 methylene groups. Points 8 and 9 are the binding constants of the DFO complexes and the protonated complexes of DFO. Point 10 is mesitylenetrihydroxamic acid. The filled triangles represent compounds from the current invention. Point 11 represents the complexes of Ligand 1, point 12 represents the protonated complexes of Ligand 1, and point 13 represents the complexes of Ligand 7.

The present invention relates generally to novel chelating compounds having a general formula of $$R^1-N(R^2)-R^3$$

wherein $R^1$=hydrogen or tosylate, $R^2$=hydrogen, methyl, ethyl, n-propyl or isopropyl and
and $R^3$= a.)

wherein x, y, and z vary independently from 2 to 4, and $R^4$=hydrogen or $C_1$-$C_{10}$ straight or branched alkyl;

b.)

wherein x, y, and z vary independently from 2 to 4 and $R^4$=hydrogen or $C_1$-$C_{10}$ straight or branched alkyl;

c.)

wherein $R^4$=hydrogen or $C_1$-$C_{10}$ straight or branched alkyl;

d.)

wherein $R^4$=hydrogen or $C_1$-$C_{10}$ straight or branched alkyl;

e.)

wherein n=2 or 3, $R^5$=hydrogen or methyl, and $R^4$=hydrogen or $C_1$-$C_{10}$ straight or branched alkyl;

f.)
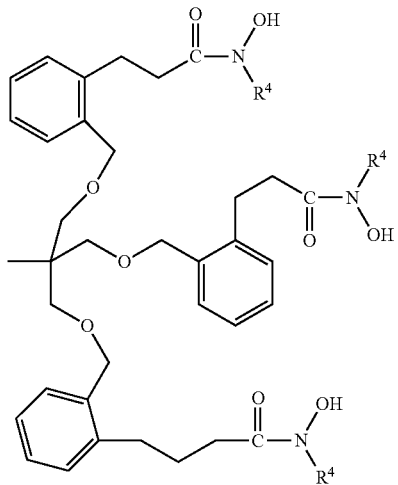

wherein $R^4$=hydrogen or $C_1$-$C_{10}$ straight or branched alkyl;

g)
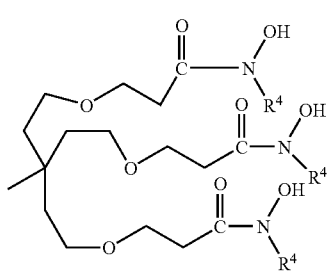

wherein $R^4$=hydrogen or $C_1$-$C_{10}$ straight or branched alkyl; and h.)
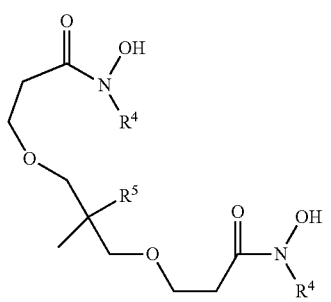

wherein $R^5$=hydrogen or methyl and $R^4$=hydrogen or $C_1$-$C_{10}$ straight or branched alkyl.

The novel compounds of the present invention are particularly useful as chelators or chelating agents. One preferred use of the free ligands would be in vivo chelation therapy to remove metal ions such as $Fe^{3+}$ and $Al^{3+}$ from the body.

The compounds include an amine functional group that allows the ligands to be easily linked to an insoluble matrix via a sulfonamide linkage, an amide linkage or a urea linkage to provide immobilized, tethered chelators. Typically, the insoluble matrix comprises a resin support. The resin support may take the form of a macro-porous polystyrene such as commercially available under the trademark XAD-4 sold by Rohm and Haas. Other polymer resins useful in the present invention include but are not limited to, polyacrylate, sepharose and silica gel.

The overall process of adding a chelating compound of the present invention to a polystyrene resin via a sulfonamide bond is shown in Scheme 1, where $NR^2H$-Ligand in this and subsequent schemes refers to the free amine form ($R^1$=H; $R^2$=hydrogen, methyl, ethyl, n-propyl or isopropyl) of any of the free ligands represented by $R^3$=a through h.

Scheme 1

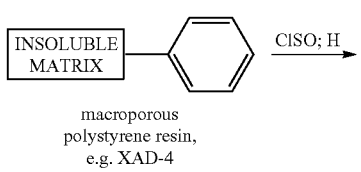

macroporous polystyrene resin, e.g. XAD-4

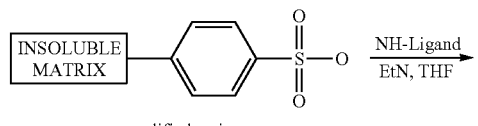

modified resin

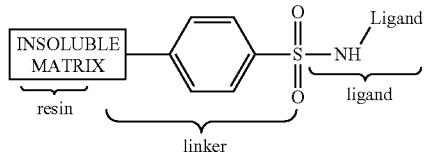

The overall process of adding a chelating compound of the present invention to a resin support by means of an amide linkage is shown in Scheme 2.

Scheme 2

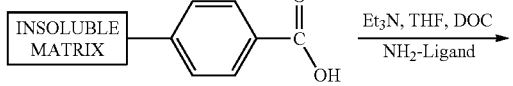

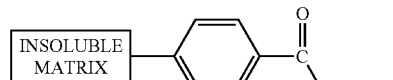

The overall process of adding a chelating compound of the present invention to a resin support by means of a urea linkage is shown in Scheme 3.

Scheme 3

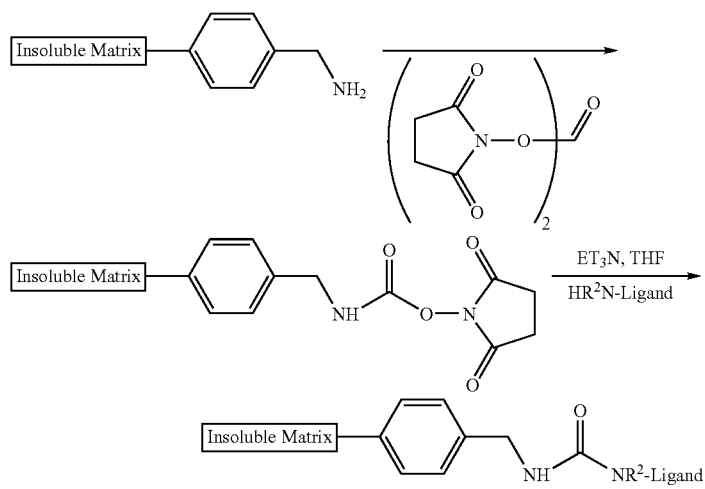

For certain applications it may be desirable to elongate the linker by adding polyethylene glycol units between the resin support and the ligand in order to increase the rate of metal binding to the resin-bound ligand. These elongated linkers are added using commercially available amine capped polyethylene glycols of variable length, with the use of a urea functional group to covalently bind the ligand and linker moieties.

The elongation process is illustrated in Scheme 4 using the linker 3-oxa-1,5-pentanediamine as a specific example.

Other commercially available amine-capped polyethyleneglycols include the compounds

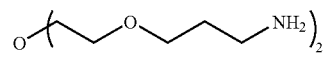

Scheme 4

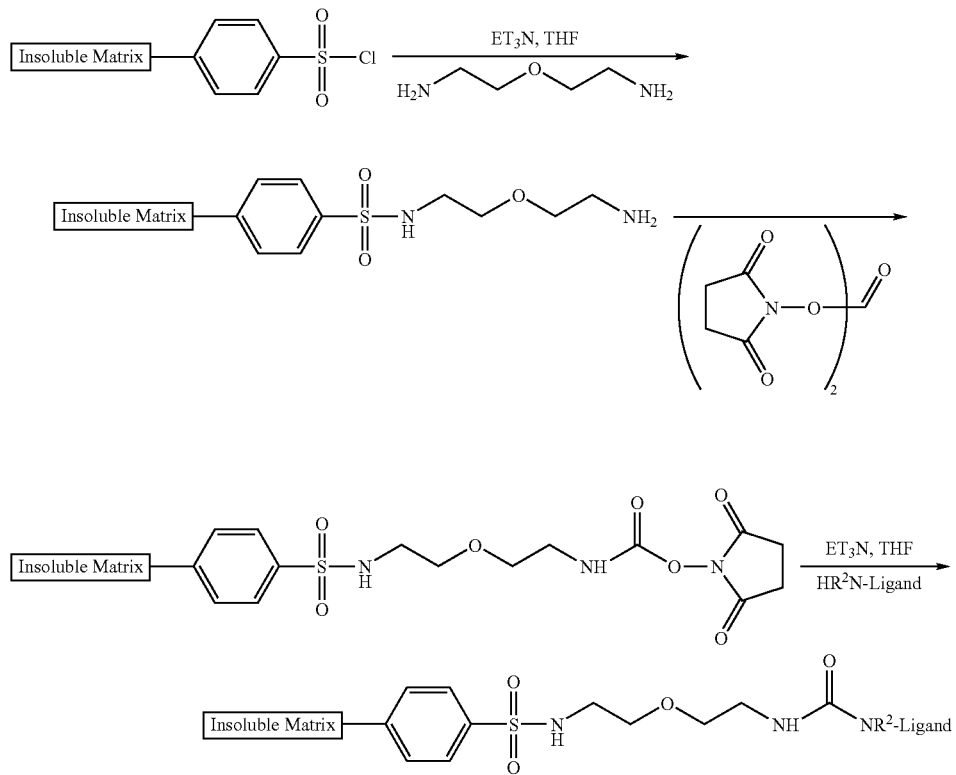

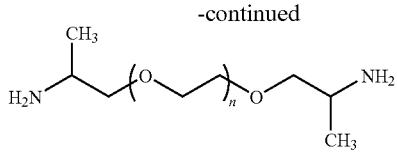

n = 10-12 which give chelating resins with the structures shown below

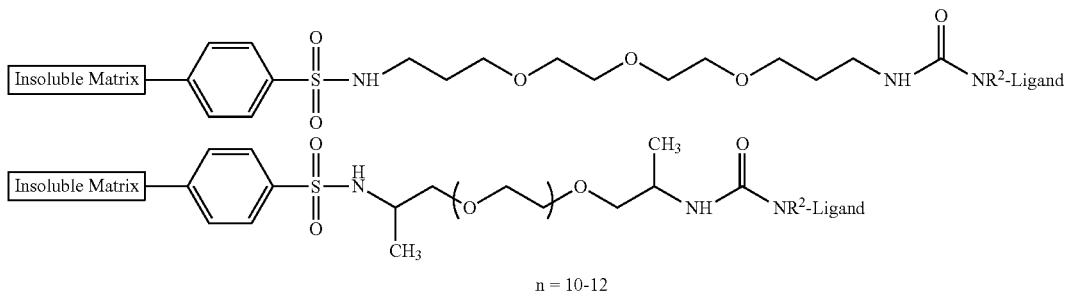

n = 10-12

The immobilized, tethered chelators of the present invention comprise the chelating compounds identified above bound to a resin support through an appropriate linkage. The immobilized, tethered chelators of the present invention may be generally described as having the following formula:

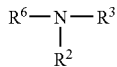

wherein $R^6$=

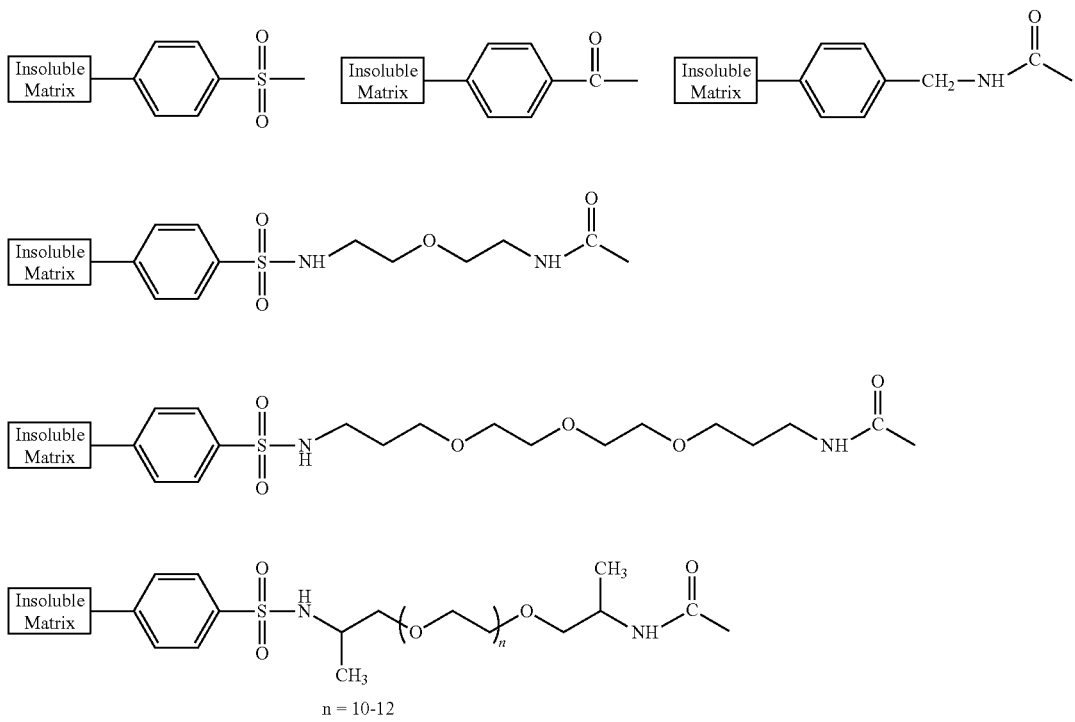

n = 10-12

$R^2$=hydrogen, methyl, ethyl; n-propyl or isopropyl and $R^3$=

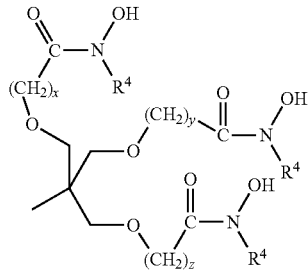

a.)

wherein x, y, and z vary independently from 2 to 4 and $R^4$=hydrogen or $C_1$-$C_{10}$ straight or branched alkyl;

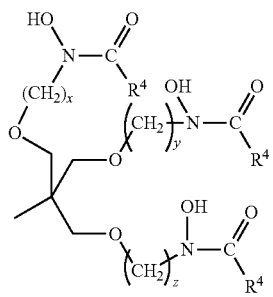

b.)

wherein x, y, and z vary independently from 2 to 4, and $R^4$=hydrogen or $C_1$-$C_{10}$ straight or branched alkyl;

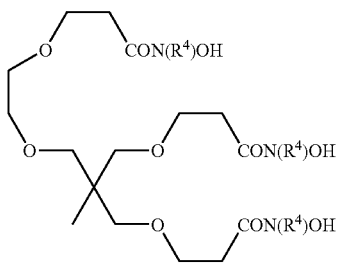

c.)

wherein $R^4$=hydrogen or $C_1$-$C_{10}$ straight or branched alkyl;

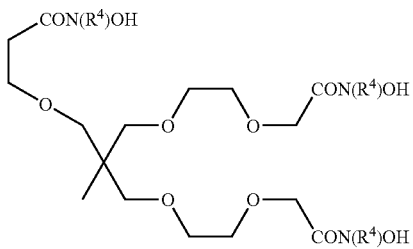

d.)

wherein $R^4$=hydrogen or $C_1$-$C_{10}$ straight or branched alkyl;

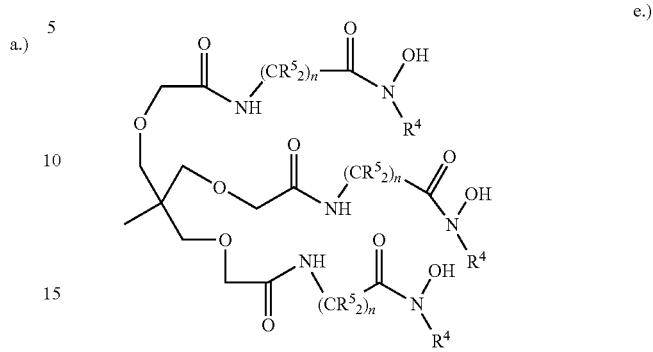

e.)

wherein n=2 or 3, $R^5$=hydrogen or methyl, and $R^4$=hydrogen or $C_1$-$C_{10}$ straight or branched alkyl;

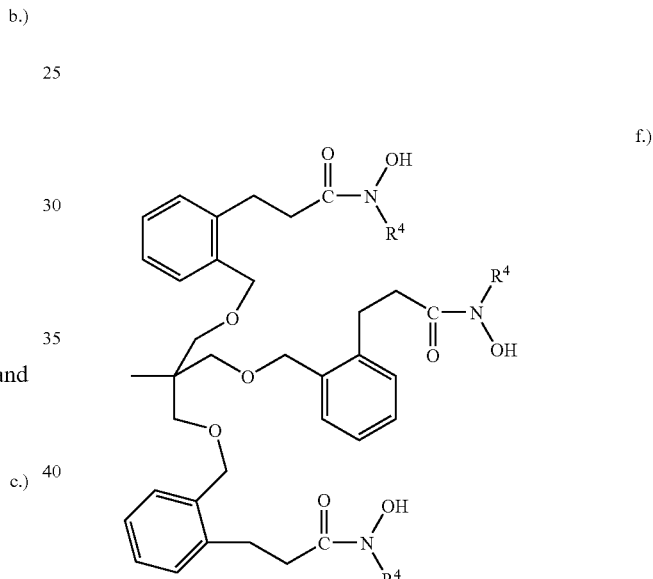

f.)

wherein $R^4$=hydrogen or $C_1$-$C_{10}$ straight or branched alkyl;

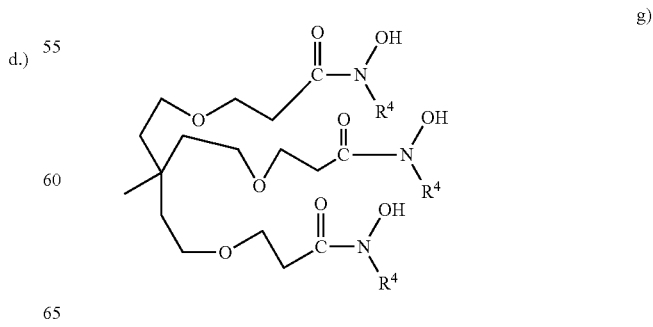

g)

wherein $R^4$=hydrogen or $C_1$-$C_{10}$ straight or branched alkyl; and h.)

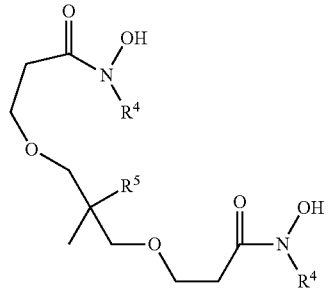

wherein $R^5$=hydrogen or methyl and $R^4$=hydrogen or $C_1$-$C_{10}$ straight or branched alkyl.

Preparation of Compounds of this Invention

Selected chelating agents and chelating resins from this invention are listed in Table 1.

TABLE 1

Partial list of chelating agents and chelating resins included in this invention

| | $R^3$ | x | y | z | $R^2$ | $R^5$ |
|---|---|---|---|---|---|---|
| Free Ligands ($R^1$ = Tosyl, $R^4$ = H) | | | | | $R^1$—N—$R^3$ $\mid$ $R^2$ | |
| Ligand | | | | | | |
| Ligand 1 | a | 2 | 2 | 2 | H | |
| Ligand 2 | a | 3 | 3 | 3 | H | |
| Ligand 3 | a | 4 | 4 | 4 | H | |
| Ligand 4 | a | 4 | 4 | 2 | H | |
| Ligand 5 | c | | | | H | |
| Ligand 6 | d | | | | H | |
| Ligand 7 | h | | | | | Methyl |
| Ligand 8 | a | 3 | 3 | 2 | H | |
| Ligand 9 | g | | | | | |
| Resins ($R^6$ = polystyrenesulfonate, $R^4$ = H) | | | | | $R^6$—N—$R^3$ $\mid$ $R^2$ | |
| Resin 1 | a | 2 | 2 | 2 | H | |
| Resin 2 | h | | | | | Methyl |

EXAMPLE 1

Synthesis of Ligand 1

The overall synthesis of Ligand 1 is shown in Scheme 5. The aminotriol (1, Tris buffer) was reacted with acrylonitrile in the presence of a catalytic amount of base to give the trinitrile (Intermediate I) (Newkome, G. R. and X. Lin, *Symmetrical, four-directional, poly(ether-amide) cascade polymers*. Macromolecules, 1991, 24(6): 1443-1444). Reaction of Intermediate 1 in refluxing methanolic HCl gave the tris(methyl ester) (Intermediate 2). Reaction of Intermediate 2 with tosyl chloride gave the sulfonamide tris ester (Intermediate 3). This ester was converted to the trihydroxamic acid (Ligand 1) by reaction with O-trimethylsilyl hydroxylamine in methanol.

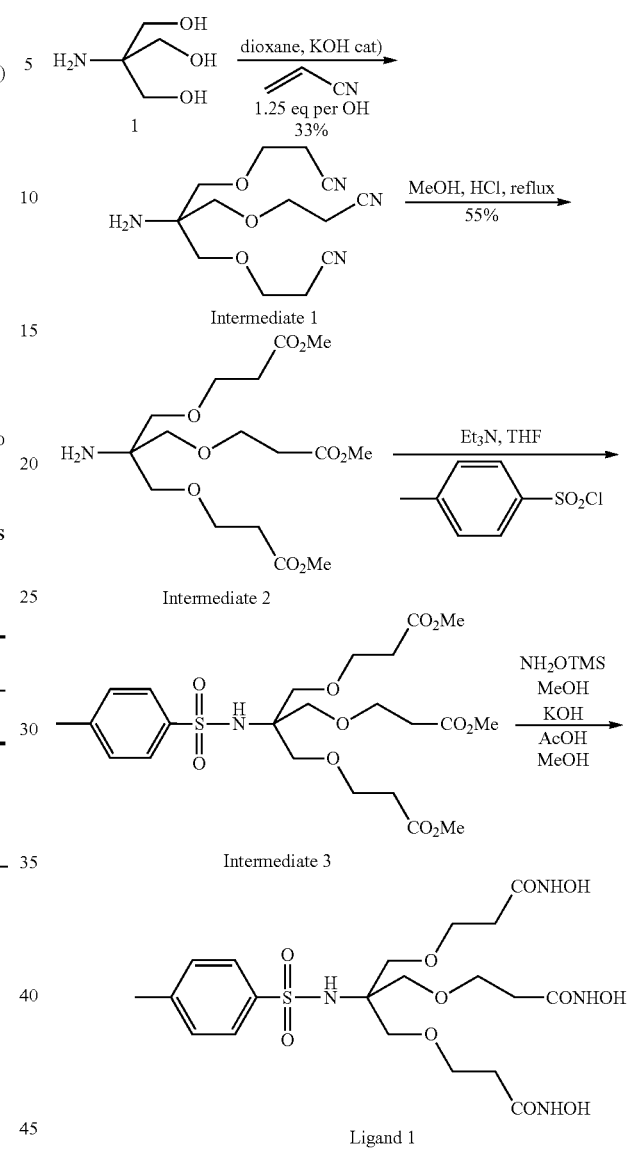

Synthesis of Intermediate 1

To a stirred solution of tris(hydroxymethyl)aminomethane (50.0 g, 412.0 mmol) and KOH (2.3 g, 4.5% of the weight of alcohol) in 1,4-dioxane(150 mL) was added acrylonitrile (71.17 g, 1342.4 mmol) drop wise over a period of 1 h, after which a clear solution was obtained. After stirring at room temperature for 24 h, the mixture was made acidic (~pH=2) by the addition of dil. HCl. After extraction with $CH_2Cl_2$ (3×100 mL) the combined organic layers were dried over sodium sulfate and evaporated to give tris[(cyanoethoxy)methyl]aminomethane (Intermediate 1), 43:2 g (33.5%). IR (neat) 3588, 3368, 2251 cm$^{-1}$; $^1$H NMR (CDCl$_3$) δ 3.68 (t, J=6.0 Hz, 6H), 3.44 (s, 6H), 2.61 (t, J=6.0 Hz), 1.68 (br s, 2H); $^{13}$C NMR (CDCl$_3$) δ 118.2, 72.7, 65.9, 56.3, 19.0; HMS (EI, MH$^+$) calcd for $C_{13}H_{21}N_4O_3$: 281.16147, found: 281.16138. (Newkome, G. R. and X. Lin, *Symmetrical, four-directional, poly(ether-amide) cascade polymers*. Macromolecules, 1991. 24(6): p. 1443-1444.

Synthesis of Intermediate 2

Dry HCl gas was passed through a solution of intermediate 1 (52.6 g, 187.0 mmol) in dry methanol (150 mL) until the solution was saturated with HCl. The mixture was refluxed overnight. After the solution was cooled, $NH_4Cl$ was removed by filtration, and the filtrate was concentrated to give a gum. The gum was taken up in THF, filtered, and the filtrate was concentrated to get the tris ester (Intermediate 2) 37.0 g (55.0%). IR (neat) 3394, 1735 cm$^{-1}$; $^1$H NMR (CDCl$_3$) δ 3.69 (t, $^2J_{h-h}$=6.31 Hz, 6H), $^{13}$C NMR (CDCl$_3$) δ 172.4, 69.0, 67.1, 59.6, 52.0, 34.7; HMS (El, MH$^+$) calcd for $C_{16}H_{30}NO_9$: 380.19217, found: 380.19205. (Nierengarten, J. F.; Habicher, T.; Kessinger, R.; Cardullo, F., Djuederich, F.; Gramlich, V.; Gisselbrecht, J. P.; Boudon, D.; Gross, M., *Macrocylization on the fullerene core. Direct regio- and diasterioselective multi-functionalization of [60]fullerene, and synthesis of fullerene-dendrimer derivatives*. Helv. Chim. Acta, 1997, 80: 2238-2276).

Synthesis of Intermediate 3

To a stirred solution of tosyl chloride (10.0 g, 52.4 mmol) and the tris ester (Intermediate 2) (19.90 g, 52.4 mmol) in CH$_2$Cl$_2$ was added NEt$_3$ (6.37 g, 62.9 mmol) and the mixture was heated at reflux overnight. The solvent was removed in vacuo, and the residue was redissolved in CH$_2$Cl$_2$ (200 mL) and washed with water (3×100 mL). The organic layer was dried over Na$_2$SO$_4$ and concentrated to give a gum. Column chromatography using silica gel with 50% ethyl acetate in hexane yielded a gummy solid of Intermediate 3 (20.4 g, 73%), which later crystallized on storing at room temperature. Finally it was characterized by X-ray crystallography. IR (neat) 3610, 3287, 1736 cm$^{-1}$; $^1$H NMR (CDCl$_3$) δ 7.78, 7.76, 7.27, 7.24 (s each, 4H), 3.68 (s, 9H), 3.51 (s, 6H), 3.51 (t, $^2J_{h-h}$=6.5 Hz, 6H), 2.41 (t, $^2J_{h-h}$=6.5 Hz, 6H) 2.41 (s, 3H); $^{13}$C NMR (CDCl$_3$) δ 172.1, 142.8, 140.5, 129.2, 127.0, 69.9, 66.7, 62.4, 51.9, 34.7, 21.6; HMS (El, MH$^+$) calcd for $C_{23}H_{36}NO_{11}S$: 534.20095, found: 534.20093.

Synthesis of Ligand 1

To a stirred solution of the tris(ester) (Intermediate 3) (8.23 g, 15.4 mmol) in methanol (100 mL) was added NH$_2$OTMS (9.74 g, 92.5 mmol) followed by KOH (2.60 g, 46.0 mmol); After 6 h at room temperature, the reaction mixture was treated with 20 g of prewashed Amberlyst-15 and swirled for 1 h. The resin was filtered off and the filtrate was evaporated to give a gum. Recrystallization from acetone:hexane (1:1) yielded the tris hydroxamate (Ligand 1), 5.02 g, (61%) which was characterized by X-ray crystallography. IR (neat) 3184, 1631 cm$^{-1}$; $^1$H NMR (CDCl$_3$) δ 7.76, 7.73, 7.42, 7.39 (s each, 4H), 3.46 (t, J=5.8 Hz, 6H), 3.40 (s, 6H), 3.31 (s, 3H, MeOH), 2.40 (s, 3H), 2.30 (t, J =5.8 Hz, 6H); $^{13}$C NMR (CDCl$_3$) δ 171.1, 145.0, 139.0, 130.1, 127.0, 69.2, 67.0, 63.0, 49.2 (CH$_3$OH), 33.3, 21.0 HMS (El, MH$^+$) calcd for $C_{20}H_{33}N_4O_{11}S$: 537.18677, found: 537.18665.

EXAMPLE 2

Synthesis of Ligand 2

The overall synthesis of Ligand 2 is shown in Scheme 6. The trimethyl orthoester of 4-iodo-1-butyric acid (3), in which the vulnerable sp$^3$ carbon has been protected, is known to alkylate alkoxides (Srivastava, R. P., Hajda, J. *Stereospecific synthesis of ether phospholipids. Preparation of 1-O-(3'-carboxypropyl)-glycero-3-phosphoserine from glyceric acid*. Tetrahedron Lett. 1991, 32, 6525-6528) (Method A). Thus treatment of the BOC-protected triol (2) with sodium hydride and the trimethyl ortho ester (3) in DMF, followed by deprotection with anhydrous methanolic HCl gives the triester (Intermediate 4). Alternatively, reductive alkylation of the trimethylsilylated triol (BSA, reflux) with 3-cyanopropionaldehyde (Iwanami, K., Kentaro Y., Takeshi, O. *An Efficient and Convenient Method for the Direct Conversion of Alkyl Silyl Ethers into Corresponding Alkyl Ethers Catalyzed by Iron (III) Chloride*. Synthesis 2005, 2669-2672) (Method B), followed by treatment with anhydrous HCl in refluxing methanol should also yield intermediate 4. Intermediate 4 is tosylated to give Intermediate 5, which is then converted to the corresponding hydroxamic acid (Ligand 2) by treatment with O-(trimethylsilyl)hydroxylamine)

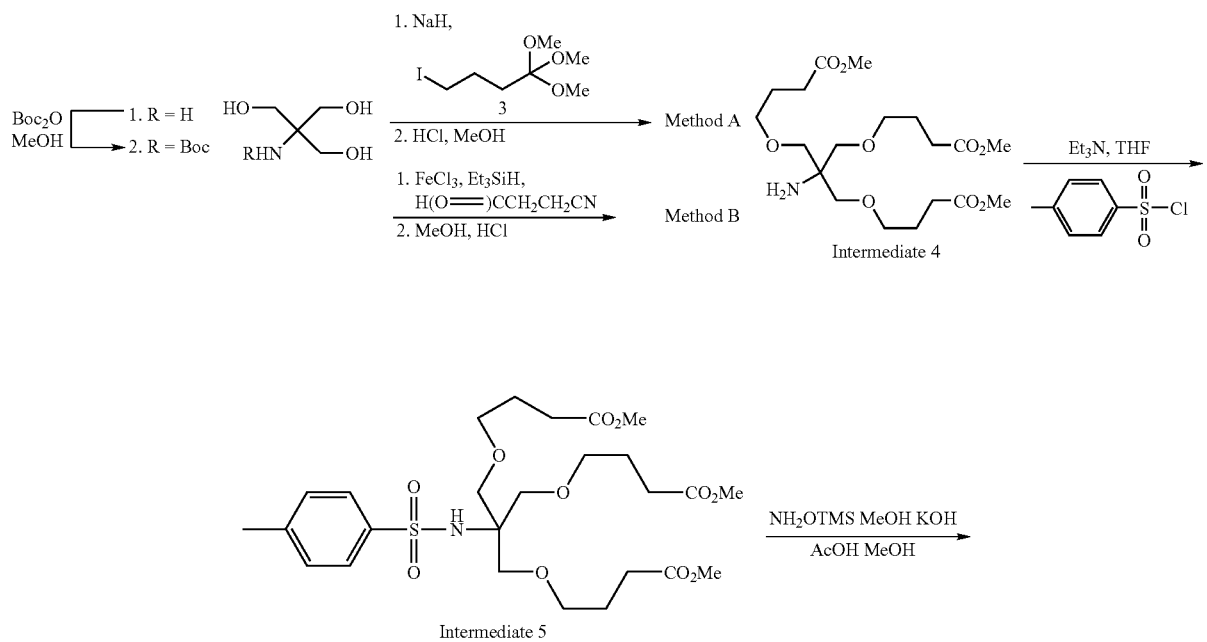

Scheme 6

-continued

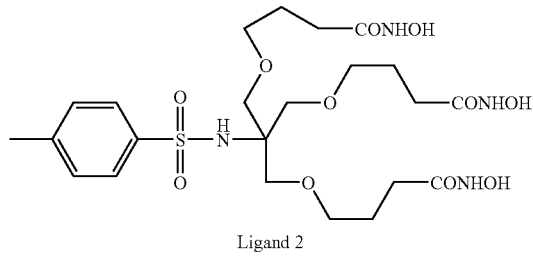
Ligand 2

EXAMPLE 3

Synthesis of Ligand 3.

The overall synthesis of Ligand 3 is shown in Scheme 7. Treatment of the BOC-protected triol (2) with sodium hydride and the trimethyl ortho ester or 5-iodo-1-pentanoic acid (4) in DMF, followed by deprotection with anhydrous methanolic HCl gives the triester (Intermediate 6). Alternatively, reductive alkylation of the trimethylsilylated triol (BSA, reflux) with 4-cyanobutryoaldehyde (Iwanami, K., Kentaro Y., Takeshi, O. *An Efficient and Convenient Method for the Direct Conversion of Alkyl Silyl Ethers into Corresponding Alkyl Ethers Catalyzed by Iron (III) Chloride*. Synthesis 2005, 2669-2672) (Method B), followed by treatment with anhydrous HCl in refluxing methanol should also yield intermediate 6. Intermediate 6 is tosylated to give Intermediate 7, which is then converted to the corresponding hydroxamic acid (Ligand 3) by treatment with O-(trimethylsilyl) hydroxylamine)

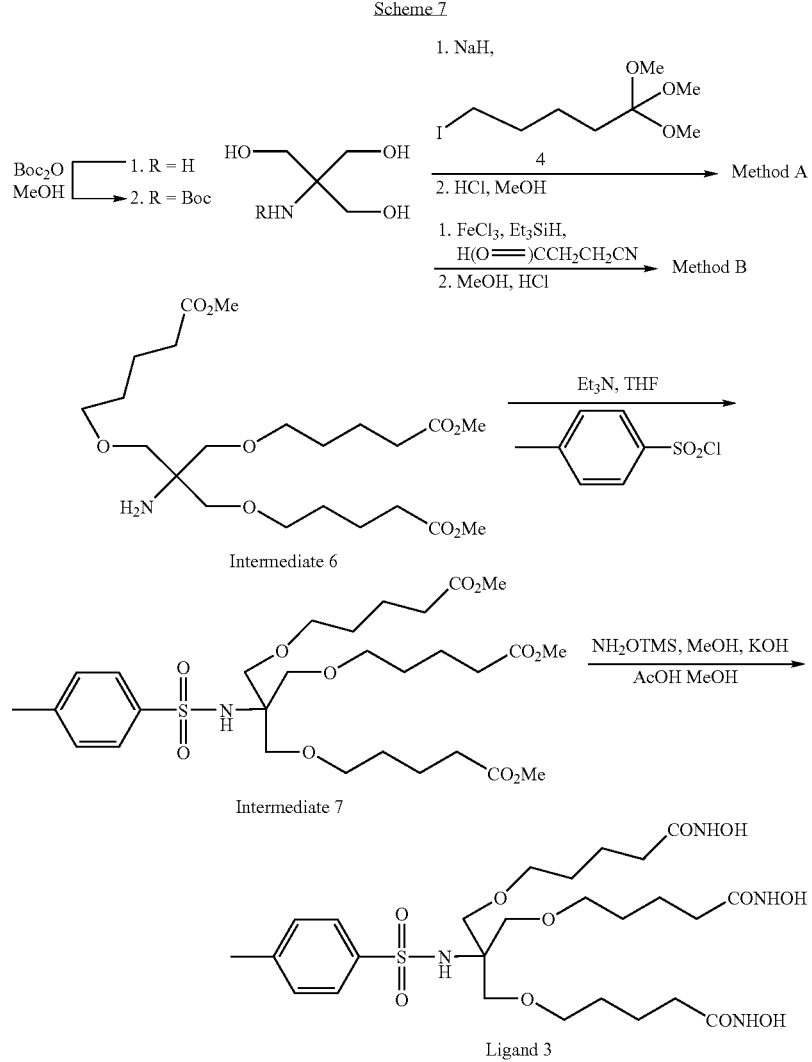

EXAMPLE 4

Synthesis of Ligand 4. The binding constants for Ligand 1 (see below) indicate that two arms of the ligand bind to metal ions very strongly, but that steric hindrance weakens the binding of the third arm. In the heteropodal Ligand 4, the length of two of the ligand arms have been extended to relieve this internal strain. The synthesis of ligand 4 is shown in Scheme 8. To prepare heteropodal trihydroxamic ligands, two of the hydroxyls on the aminotriol(tris) are first blocked by a protecting group. The aminotriol (1) is converted to the known cyclic acetal (5) using a published 2 step, 1 pot procedure (Ooi, H., Ishibashi, N., Iwabuchi, U., Ishihara, J., Hatakeyama, S. *A concise Route to (+)-Lactacystin*. J. Org. Chem. 2004, 69, 7765-7768). Alternatively, the diol can be protected as the benzylidene (6a) (Balakumar, V., *A highly regio- and chemoselective reductive cleavage of benzylidene acetals with EtAlCl$_2$-Et$_3$SiH*, Synlet, 2004, 647-650; Low, J. N., B. F. Milne, J.-N. Ross, and J. L Wardell, *Derivatives of N,N'-bis[2-Hydroxy-1,1-bis(hydroxymethyl)ethyl] ethanediamide*. Journal of the Brazilian Chemical Society, 2002, 13: 207-217) using similar reaction conditions, which results in additional options for deprotection later in the synthetic sequence. Addition of the remaining free alcohol to acrylonitrile yields the mononitrile (7) (Newkome, G. R., Lin, X. *Symmetrical, four-directional, poly(ether-amide) cascade polymers*. Macromolecules. 1991, 24, 1443-1444). Simultaneous deprotection of the acetal and methanolysis of the nitrile with a refluxing solution of methanolic HCl yields the monoester-diol (8). The diol is then alkylated by the addition of the trimethyl ortho ester of 5-iodopentanoic acid to form the triester (Intermediate 8). An additional complication in the alkylation of the monoester diol is base-catalyzed beta elimination of the alkoxy group beta to the ester. Intermediate 8 is tosylated to give Intermediate 9, which is converted to the corresponding trihydroxamate (Ligand 4) by the addition of O-(trimethylsilyl)hydroxylamine.

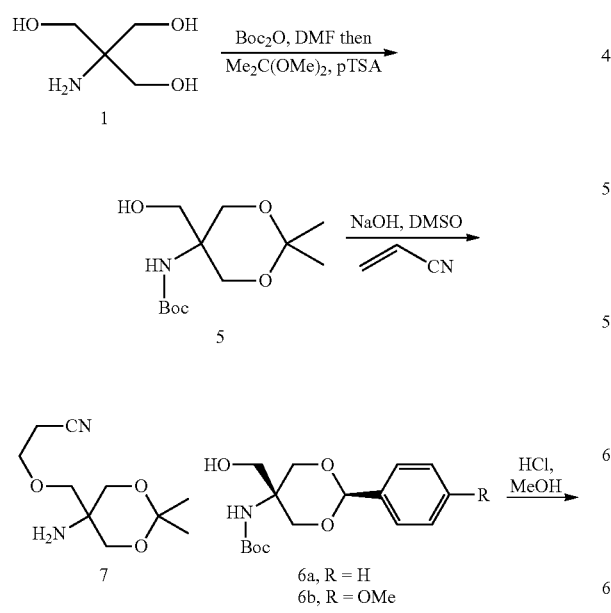

Scheme 8

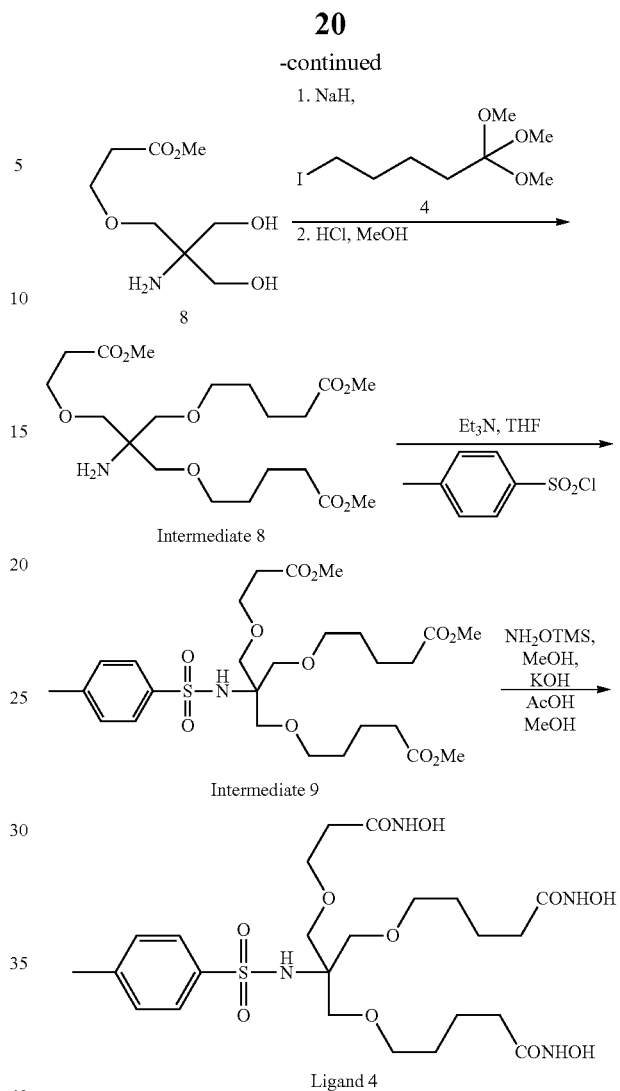

EXAMPLE 5

Synthesis of Ligand 5. The synthesis of the heteropodal Ligand 5 is described in Scheme 9. The extension of one arm of the ligand is achieved by the reaction of the acetal protected aminotriol (5) with chloroacetic acid, followed by selective reduction of the carboxylic acid and deprotection of the cyclic acetal to give the unsymmetric triol (9). Adding the triol to acrylonitrile gives the trinitrile Intermediate 10, and methanolysis of the nitrile gives the tris(ester) (Intermediate 11). This compound is tosylated to give Intermediate 12. The addition of O-(trimethylsilyl)hydroxylamine to Intermediate 12 gives the heteropodal Ligand 5.

Scheme 9

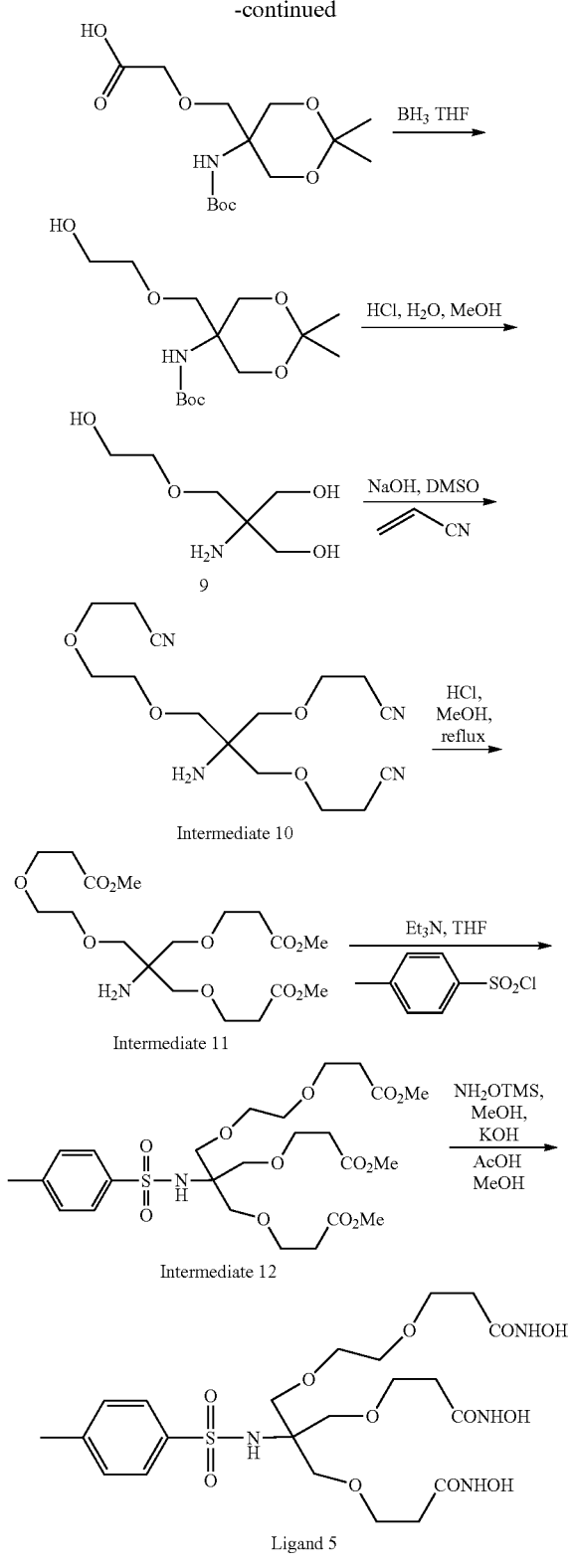

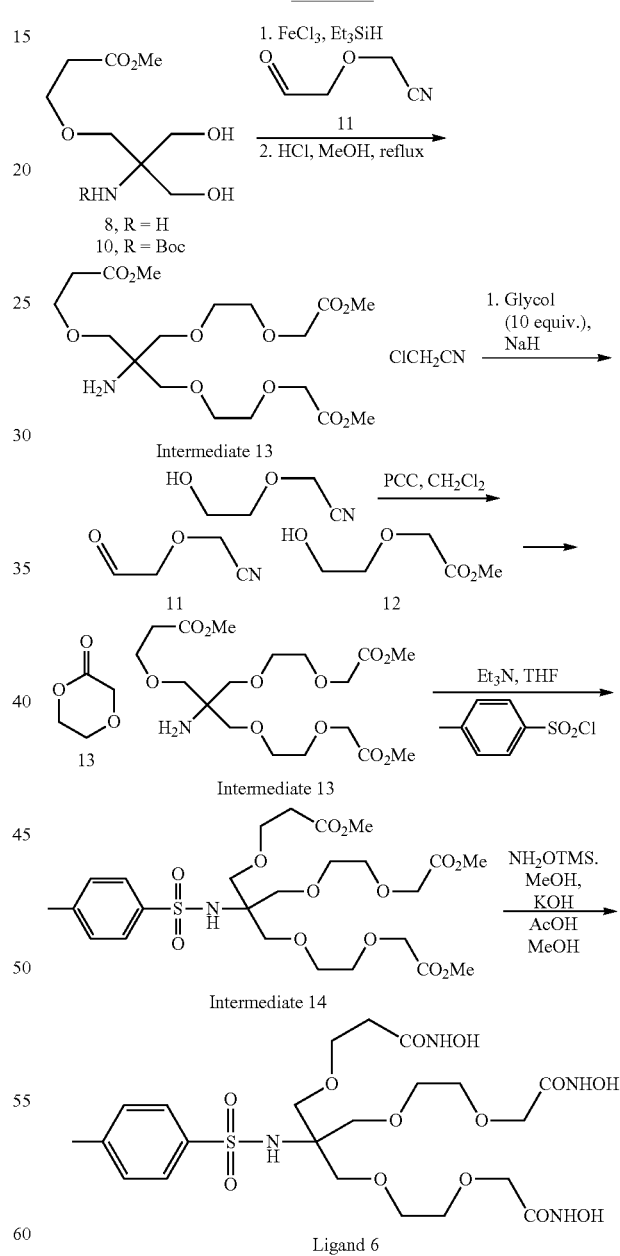

group to give (10). The remaining hydroxyls are reductively alkylated with aldehyde (11) followed by methanolysis to yield the triester (Intermediate 13). The aldehyde (11) is easily prepared in two steps from glycol. Although synthesis of the ester (12) would provide a more direct approach, the reaction would be complicated by competing, rapid lactonization to lactone (13). Intermediate 13 is tosylated to give intermediate 14. This compound is treated with O-(trimethylsilyl)hydroxylamine to give the heteropodal trishydroxamic acid Ligand 6.

EXAMPLE 6

Synthesis of Ligand 6

The synthesis of Ligand 6 is shown in Scheme 10. The diol (8) from Scheme 8 is reprotected at the amine with a Boc

EXAMPLE 7

Synthesis of Ligand 7. The overall synthesis of Ligand 7 is shown in Scheme 11.

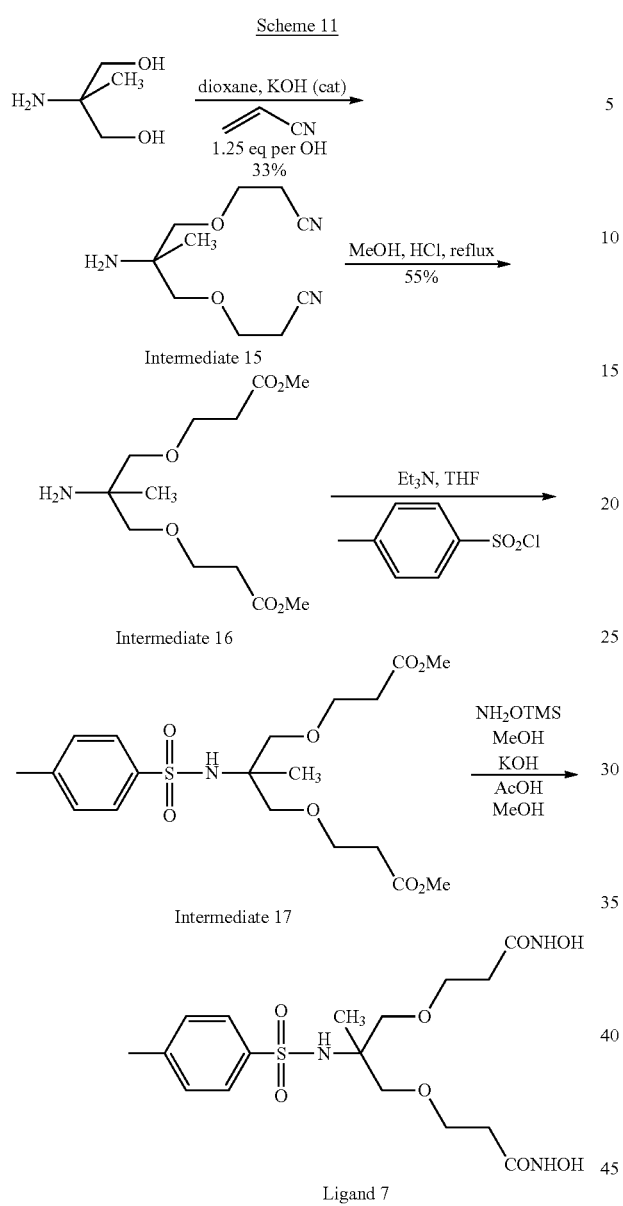

Scheme 11

Intermediate 15

Intermediate 16

Intermediate 17

Ligand 7

Synthesis of Intermediate 15

To a stirred solution of 2-amino-2-methyl-1,3-propanediol (50.0 g, 475.5 mmol) and KOH (1.0 g, 2% of the weight of diol) in 1,4-dioxane (100 mL) was added acrylonitrile (56.7 g; 1070.0 mmol) dropwise over a period of 1 h, after which a clear solution was obtained. After stirring at room temperature for 24 h, 200 mL of $CH_2Cl_2$ was added to the mixture. The mixture was extracted with water and the organic layer was dried over sodium sulfate. The solvent was evaporated to yield a thick oil. Distillation under reduced pressure (160 °C/10 mm Hg) yielded Intermediate 15, 39.5 g (39%). IR (neat) 3517, 3360, 2250 cm$^{-1}$; $^1$H NMR (CDCl$_3$) δ 3.68 (t, J=6.1 Hz, 4H), 3.33 (Abq, Δv=14.2 Hz, J=8.5 Hz, 4H), 2.60 (t, J=6.1 Hz, 4H), 1.44 (br s, 2H), 1.06(s, 3H; $^{13}$C NMR (CDCl$_3$) δ 118.2, 76.5, 65.8, 52.8, 22.6, 19.0 HMS (El, MH$^+$) calcd for $C_{10}H_{18}N_3O_2$: 212.14002, found: 212.13989.

Synthesis of Intermediate 16

Dry HCl gas was passed through a solution of Intermediate 16 (39.48 g, 186.1 mmol) in dry methanol (150 ml) until the solution was saturated with HCl. The mixture was refluxed overnight. After cooling, NH$_4$Cl was removed by filtration, and the filtrate was concentrated to give a gum. The gum was redissolved in THF, filtered, and the filtrate was concentrated to get the diester (Intermediate 16) 30.0 g (57.0%). IR (neat) 3409, 1727 cm$^{-1}$; $^1$H NMR (CDCl$_3$) δ 3.79 (t, J=6.1 Hz, 2H), 3.70 (2, 6H), 3.62 (s, 4H), 2.64 (t, J=6.1 Hz, 4H), 1.42 (s, 3H); $^{13}$C NMR (CDCl$_3$) δ 172.6, 71.7, 67.2, 58.0, 52.1, 34.8, 18.4; HMS (El, MH$^+$) calcd for $C_{12}H_{24}NO_6$: 278.16047, found: 278.16037.

Synthesis of Intermediate 17

To a stirred Solution of tosyl chloride (10.0 g, 52.4 mmol) and Intermediate 16 (14.54 g, 52.4 mmol) in $CH_2Cl_2$ was added NEt$_3$ (6.37 g, 62.9 mmol) and the mixture was heated at reflux overnight. The solvent was removed in vacuo, and the residue was redissolved in $CH_2Cl_2$ (200 mL) and washed with water (3×100 mL). The organic layer was dried over Na$_2$SO$_4$ and concentrated to give a gum. Column chromatography using silica gel with 40% ethyl acetate in hexane yielded a gummy solid of Intermediate 17, (16.9 g, 74%). IR (neat) 3604, 1736, 1735 cm$^{-1}$; $^1$H NMR (CDCl$_3$) δ 7.82, 7.55, 7.29, 7.26 (s each, 4H), 3.70 (s, 6H), 3.65 (t, J=6.2 Hz, 4H), 3.33 (Abq, Δv=47.0 Hz, J=9.1 Hz, 4H), 2.53 (t, J=6.2 Hz, 4H), 2.41 (s, 3H), 1.10 (s, 3H); $^{13}$C NMR (CDCl$_3$) δ 172.2, 143.1, 140.7, 129.6, 127.0, 73.7, 66.8, 58.9, 51.9, 34.9, 21.7, 18.2; HMS (El, MH$^+$) calcd for $C_{19}H_{30}NO_8S$: 432.16931, found: 432.16922.

Synthesis of Ligand 7

To a stirred solution of the ester (Intermediate 17) (3.61 g, 8.3 mmol) in methanol (50 mL) was added NH$_2$OTMs (3.52 g, 33.4 mmol) followed by KOH (0.94 g, 16.7 mmol). After 6 h at room temperature, the mixture was treated with 7.0 g of prewashed Amberlyst-15 and swirled for 1 h. The resin was filtered off and the filtrate was evaporated to give a gum. Recrystallization from $CH_2Cl_2$:ether (1:1) yielded Ligand 7, 2.46 g, (68%). IR (neat) 3233, 1633 cm$^{-1}$; $^1$H NMR (CDCl$_3$) δ 7,76, 7.68, 7.42, 7.39 (s each, 4H), 3.54 (m, 4H), 3.35 (s, 4H), 3.30 (Abq, Δv=22.6 Hz, J=10.0 Hz, 4H), 2.40 (s, 3H), 2.34 (t, J=5.8 Hz, 6H), 1.08 (s, 3H); $^{13}$C NMR (CDCl$_3$) δ 171.1, 145.0, 139.0, 130.2, 127.0, 73.5, 67.0, 59.5, 49.3, 21.0, 18.8; HMS (El, MH$^+$) calcd for $C_{17}H_{28}N_3O_8S$: 434.15983, found: 434.15970.

EXAMPLE 8

Synthesis of Resin 1. Resin 1 was prepared by synthesizing the chelating functional group (R$^3$=a) Of Ligand 1 on the surface of a polystyrene resin. The synthesis of Resin 1 is shown in Scheme 12. Macro-porous polystyrene beads (14, Amberlite XAD-4) were reacted with chlorosulfonic acid to give the polymeric sulfonyl chloride (15) (Emerson, D. W., Emerson, R. R., Joshi, S. C., Sorensen, E. M., Turek, J. E. *Polymer-bound sulfonylhydrazine functionality. Preparation, characterization, and reactions of copoly(styrene-divinylbenzenesulfonylhydrazine)*. J. Org. Chem. 1979, 44: 4634-4640; Hu, J.-B., Zhao, G., Ding, Z.-D. *Enantioselective reduction of ketones catalyzed by polymer-supported sulfonamide using NaBH4/Me3SiCl (or BF3*OEt2) as reducing agent*. Angewandte Chemie, International Edition 2001, 40: 1109-1111). The procedures in Scheme 5 were used to prepare the methyl ester of the free amine form of ligand 1 (Intermediate 2). Addition of Intermediate 2 to the sulfonyl chloride form of the resin (15) gave the sulfonamide triester (Intermediate 18). The ester functional groups were converted to hydroxamic acids by reaction with O-trimethylsilyl hydroxylamine in methanol to give Resin 1. The successful conversion of the esters to hydroxamic acids was judged from the IR spectra. The number of ligand molecules on the surface of the resin was calculated from the S and N combustion analysis of the resin to be 0.3 mmoles ligand per gram of resin.

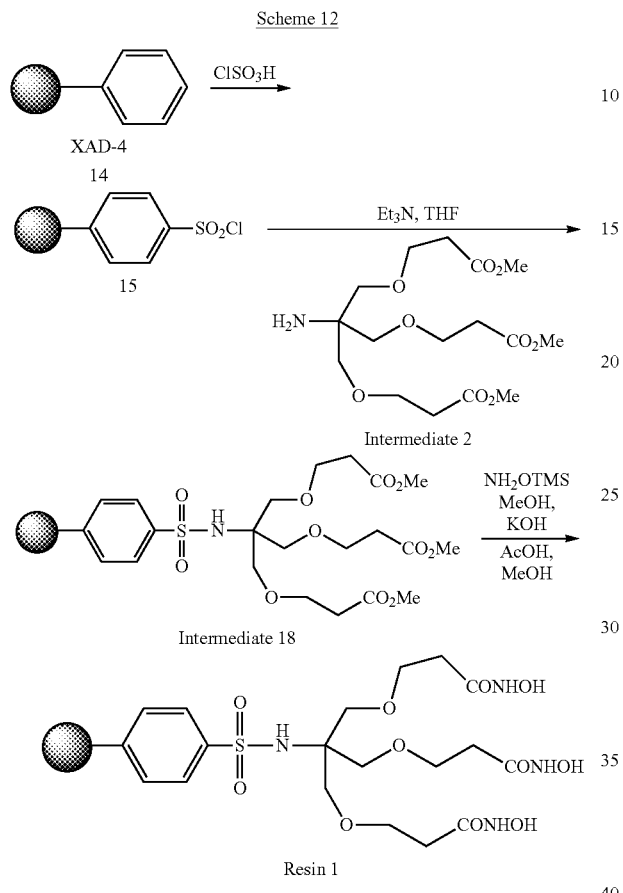

Synthesis of Sulfonyl Chloride Resin:

To 35 g of macroporous styrene-divinylbenzene, copolymer (20-60 mesh, avg. pore diameter: 40 Å, Amberlite XAD-4) in 100 mL of 1,2-dichloroethane was added 160 g (1.37 mol) of technical grade chlorosulfonic acid with occasional swirling. The mixture was kept at room temperature for 12 h. The product was filtered using a glass frit and was washed successively with two portions of dichloromethane (DCM), two portions of DCM-THF mixture, two portions of THF, and a final wash with DCM. The vacuum dried polymer was ready to use and was stored under argon at low temperature. IR (neat) 3521, 1369, 1171 $cm^{-1}$; Anal. Found: C, 57.17; H, 5.50; S, 10.23; Cl, 8.49; calculated loading S, 3.22 mmol/g, Cl, 2.39 mmol/g.

Synthesis of Intermediate 18

To polymeric sulfonyl chloride (15) (2.0 g, 5.0 mmol) in THF (50 mL) was added a solution of the tris ester of the free ligand (Intermediate 2) (7.58 g, 20.0 mmol) in THF (30 mL) followed by triethylamine (2.0 g, 20.0 mmol) and the mixture was swirled for four days at room temperature. The polymer was then filtered off and washed successively with THF, water, THF, DCM and dried in vacuo. IR (neat) 3494, 1732, 1169 $cm^{-1}$; Anal. Found: C, 58.96; H, 6.81; S, 8.22; N, 2.66; calculated loading: S, 2.57 mmol/g, N, 1.90 mmol/g.

Synthesis of Resin 1

To the resin-bound triester (Intermediate 18) (1.7 g, 4.25 mmol) in methanol (40 mL) was added $NH_2OTMs$ (4.02 g, 38.2 mmol) dropwise with stirring at room temperature. KOH (2.14 g, 38.2 mmol) was added and the mixture was swirled for 12 h. The product, resin 1, was filtered off and washed successively with methanol, water, and methanol. The resin was then swirled with dil. acetic acid for an hour and washed successively with methanol, water, THF, and dried Over pump. IR (neat) 3479, 1644, 1173 $cm^{-1}$; Anal. Found: C, 54.65 H, 5.57; S, 9.51; N, 1.59; Loading: S, 2.97 mmol/g, N, 1.14 mmol/g.

EXAMPLE 9

Synthesis of Resin 2. The overall synthesis of Resin 2 is shown in Scheme 13.

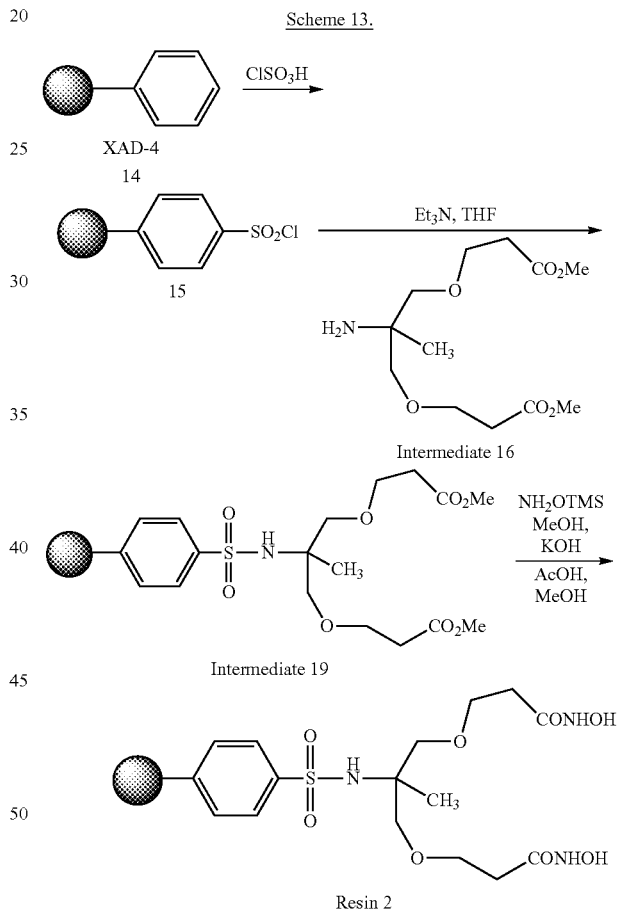

Synthesis of Intermediate 19. The synthesis of the chlorosulfonated polystyrene resin (15) is described in Scheme 12. To this polymeric sulfonyl chloride (5.2 g, 13.0 mmol) in THF (80 mL) was added a solution containing Intermediate 16 from Scheme 11, (14.4 g, 52.0 mmol) in THF (50 mL) followed by triethylamine (5.26 g, 52.0 mmol). The suspension was swirled for four days at room temperature. The product, Intermediate 19, was then filtered off and washed successively with THF, water, THF, DCM and dried over pump. IR (neat) 3492, 1735, 1170 $cm^{-1}$; Anal. Found: C, 60.28; H, 7.04; S, 8.42; N, 2.61; calculated loading: S, 2.63 mmol/g, N, 1.86 mmol/g.

Synthesis of Resin 2.

To the resin-bound diester (Intermediate 19) (5.27 g, 13.17 mmol) in methanol (60 mL) was added $NH_2OTMs$ (11.08 g, 105.3 mmol) dropwise with stirring at room temperature to give Resin 2. KOH (2.95 g, 52.6 mmol) was added and the mixture was swirled for 12 h. The resin was filtered off and washed successively with methanol, water, and methanol. The resin was then swirled with dilute acetic acid for an hour and washed successively with methanol, water, THF, and dried over pump. IR (neat) 3468, 1643, 1176 $cm^{-1}$; Anal. Found: C, 53.09 H, 5.59; S, 8.82; N, 1.95; Loading: S, 2.75 mmol/g, N, 1.39 mmol/g.

EXAMPLE 10

Ligands Immobilized via an Amide Linkage

The triester intermediate of each ligand containing a free amine group ($R^1$=H) is coupled to a resin bearing a carboxylic acid using a coupling reagent such as dicyclohexylcarbodiimide (DCC) or N-ethyl-N'-(3-dimethylaminopropyl) carbodiimide (EDC) with a tertiary amine base in THF solution. The esters are then converted to the hydroxamic acid as described above for the sulfonamide linked system. This process is described in Scheme 14 using Intermediate 2 as an example.

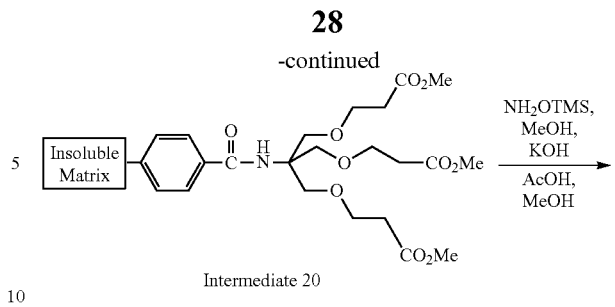

Intermediate 20

Resin 3

Scheme 14

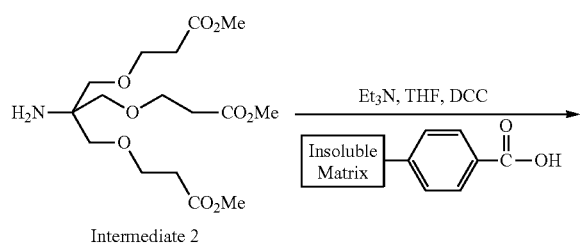

Intermediate 2

EXAMPLE 11

Ligands Immobilized via a Urea Linker

The amine of a triester intermediate is coupled to a resin bearing an amine via a urethane linkage using a reagent such as N,N-disuccinimidyl carbonate (16), carbonyl diimidazole or triphosgene with a tertiary amine base in THF solution. The esters are then converted to the hydroxamic acid as described above for the sulfonamide linked system. This process is shown in Scheme 15 using Intermediate 2 as an example.

Scheme 15

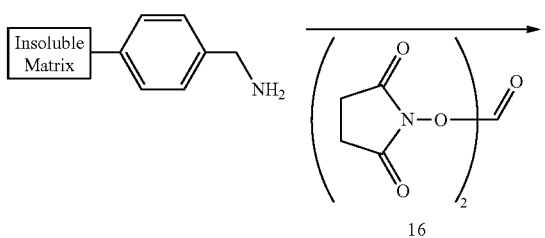

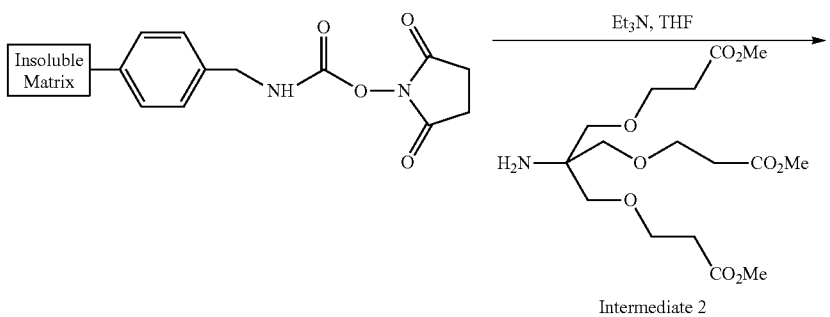

Intermediate 2

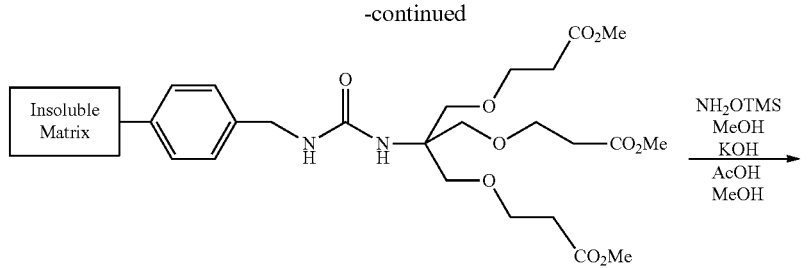

Intermediate 21

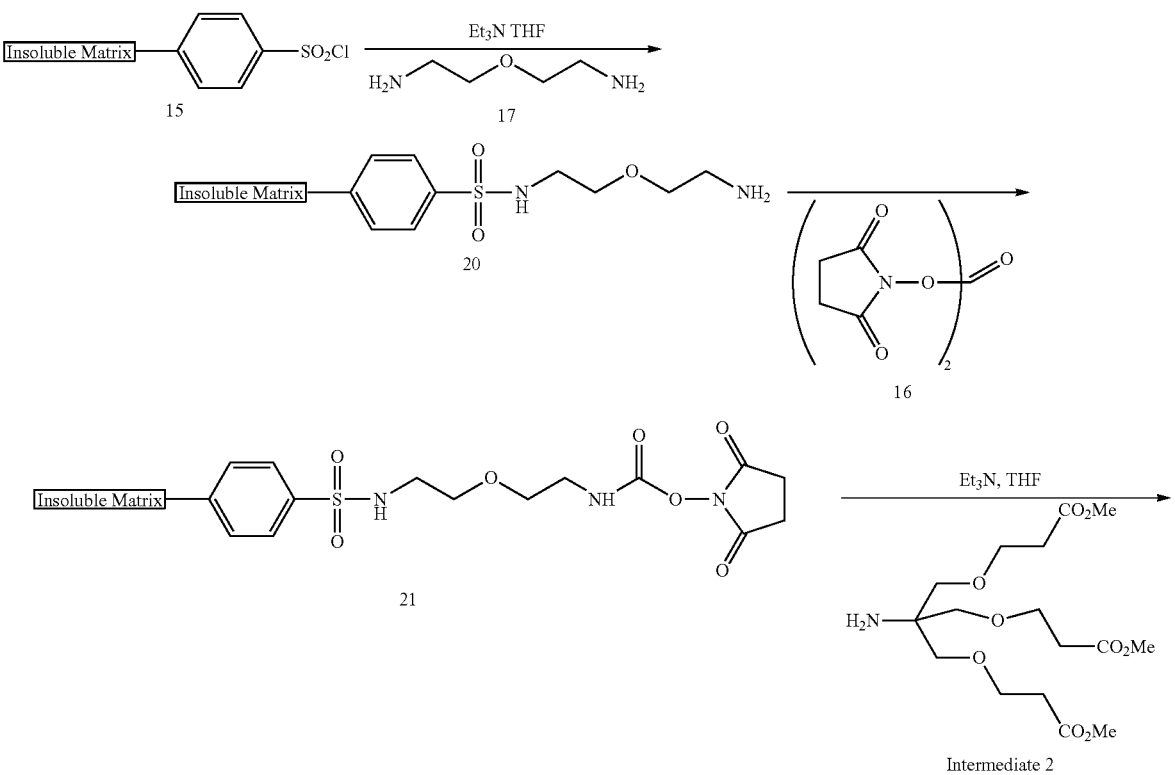

Resin 4

EXAMPLE 12

Extension of the Linker Group. In Paragraph 28 we showed three options for longer linkers that might be used to connect the chelating agent to the polymer resin. These linkers insert polyethylene glycol units between the aromatic ring of the resin and the amine group attached to the bridgehead carbon of the chelating agent.

The invention includes the use of three amine capped polyethylene glycol (PEG) based linkers, 3-oxa-1,5-diaminopentane (17), 4,7,10-trioxa-1,13-tridecanediamine (18), and the 2-aminopropane capped polyethylene glycol with 10-12 PEG units (19), all of which are commercially available in bulk. A representative attachment scheme using Intermediate 2 and the 2 PEG unit diamine (17) is shown in Scheme 16, along with the structures of the two other PEG linkers (18,19).

-continued

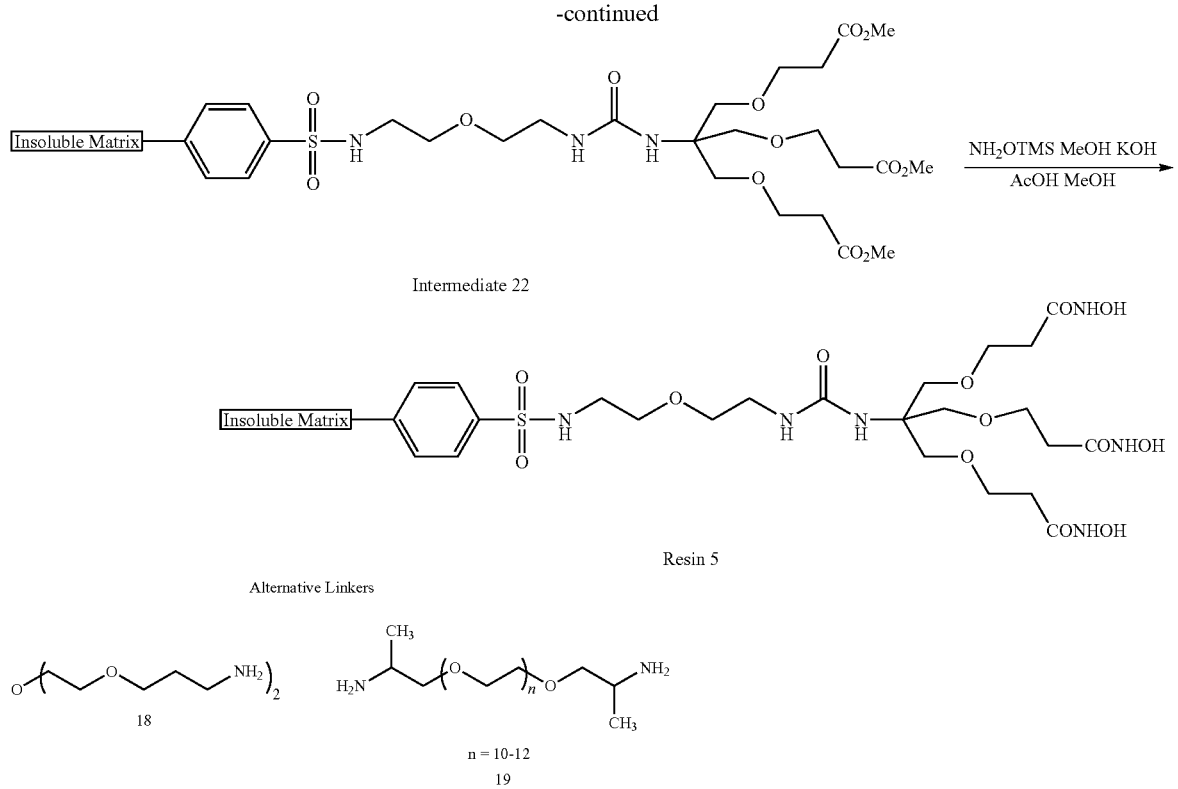

Intermediate 22

Resin 5

Alternative Linkers

18 n = 10-12
19

Each amine capped polyethylene glycol linker is attached to the activated resin (15) by using an excess of the diamine to ensure complete capping. The sulfonamide linked tether (20) is activated as the N-hydroxysuccinimide (NHS) with N,N'-disuccinimidyl carbonate (16) (Takeda, K., Y. Akagi, A. Saiki, T. Tsukahara, and H. Ogura, Studies on activating methods of functional groups. Part X. Convenient methods for syntheses of active carbamates, ureas, and nitroureas using N,N'-disuccinimido carbonate (DSC). Tetrahedron Letters, 1983, 24: 4569-4572), followed by washing to remove the excess carbonate and the N-hydroxysuccinimide byproduct from the resin to produce (21). Reaction of the activated urethane with the amino-triester (Intermediate 2) provides the resin capped product Intermediate 22 which is expected to be stable to hydroxylamine and aqueous conditions. Final conversion to the trihydroxamate (Resin 5) is accomplished with O-trimethylsilyl hydroxylamine in methanol.

EXAMPLE 13

Binding Of Metal Ions by the Free Ligands

The acid dissociation constants for the trihydroxamate Ligand 1 and the dihydroxamate Ligand 7 have been determined by potentiometric titration of the free ligands in 0.1 M $KNO_3$ at 25° C. The overall ligand protonation constants for Ligand 1 are log $\beta_{011}$=10.26, log $\beta_{012}$=19.68, and log $\beta_{013}$=28.15. The overall ligand protonation constants for Ligand 7 are log $\beta_{011}$=9.80 and log $\beta_{012}$=18.49. These protonation constants have been used in the calculations of the metal chelate stability constants described below.

The binding of $Al^{3+}$, $Fe^{3+}$, and a series of divalent metal ions to Ligand 1 has been evaluated by potentiometric titration in 0.1 M $KNO_3$ at 25° C. For most of the metal ions, two complexes were detected. In one complex, all three of the hydroxamate groups were coordinated to the central metal one. The stability of these complexes is described by the overall binding constant $$\beta_{110} = \frac{[ML]}{[M][L]} \tag{3}$$

where L refers to the fully deprotonated, trianionic form of ligand 1, and charges on the species have been omitted for clarity.

The potentiometric analysis also detected a protonated metal chelate, designated as MHL. The position of the ligand-to-metal charge transfer band in the visible spectrum of the MHL complex of $Fe^{3+}$ indicated that in the MHL complexes, two of the hydroxamate groups are coordinated to the metal ion, while the third hydroxamate group is protonated and not bound to the metal ion. The stability of the MHL complexes is described by the overall binding constant $$\beta_{111} = \frac{[MHL]}{[M][L][H]} \tag{4}$$

The calculated binding constants for the complexes of Ligand 1 are listed in Table 2. The binding constant for $Al^{3+}$ is log $\beta_{110}$=21.44. Ligands with only two hydroxamates have binding constants of about log $\beta_{110}$~15 (Evers, A., Hancock, R. D., Martell, A. E., Motekaitis, R. J., *Metal ion recognition in ligands with negatively charged oxygen donor groups. Complexation of Fe(III), Ga(III), In(III), Al(III), and other highly charged metal ions*, Inorg. Chem. 1989, 28: 2189-

2195). The larger value of log $\beta_{110}$ for Ligand 1 confirms that all three hydroxamate groups of the ligand are bound to the $Al^{3+}$.

TABLE 2

Binding constants for metal complexes of the trihydroxamate ligand, Ligand 1.

|  | $Fe^{3+}$ | $Al^{3+}$ | $Cu^{2+}$ | $Ni^{2+}$ | $Zn^{2+}$ | $Mn^{2+}$ | $Ca^{2+}$ |
|---|---|---|---|---|---|---|---|
| Log $\beta_{111}$ | 27.60 | 26.27 | 23.61 | 19.10 | 19.13 | 17.06 | 13.34 |
| Log $\beta_{110}$ | 23.78 | 21.44 | — | 10.73 | 10.13 | 8.95 | 3.71 |

The data in Table 2 confirm that Ligand 1 shows very high selectivity for the binding of trivalent metal ions such as $Al^{3+}$ and $Fe^{3+}$ in preference to the binding of $Ca^{2+}$. This is a critical property, as it allows this ligand to bind trivalent metal ions in the presence of very high concentrations of $Ca^{2+}$.

Ligand 1 showed good selectivity for $Al^{3+}$ and $Fe^{3+}$ in comparison to the divalent transition metal ions $Cu^{2+}$, $Ni^{2+}$, $Zn^{2+}$, and $Mn^{2+}$. However, the binding affinities for these metal ions were still appreciable, especially for the binding of $Cu^{2+}$. Thus it is not claimed that the invention can remove $Al^{3+}$ and/or $Fe^{3+}$ from pharmaceutical solutions without also removing significant amounts of $Cu^{2+}$ and $Zn^{2+}$. The proposed process for reducing $Al^{3+}$ in total parenteral nutrition (TPN) solutions involves the removal of $Al^{3+}$ from the calcium gluconate and sodium phosphate component solutions, rather than treating the final TPN solution. Treating the final TPN solution with the invention is likely to remove a large percentage of the essential ions $Cu^{2+}$ and $Zn^{2+}$.

EXAMPLE 14

Metal Binding by Ligand 7

The dihydroxamate Ligand 7 forms 1:1 complexes with all the metal ions studied in which both hydroxamate groups are coordinated to the metal ion. The stability of these complexes is characterized by the values of log $\beta_{110}$ shown in Table 3. The 1:1 complex of $Al^{3+}$, $Zn^{2+}$ and $Mn^{2+}$ hydrolyze to form the mixed-ligand hydroxo complexes ML(OH), characterized by the overall binding constant $$\beta_{11-1} = \frac{[ML(OH)][H]}{[M][L]} \quad (5)$$

Speciation calculations based on the stability constants in Table 3 indicated that the Al complex of Ligand 7 existed as a mixture of the ML and ML(OH) complexes over the pH range of 3 to 7. If an immobilized form of Ligand 7 (Resin 2) is used to remove $Al^{3+}$ from solutions within this pH range, the formation of the ML(OH) complex will stabilize the immobilized Al and facilitate removal of $Al^{3+}$ from the solution.

TABLE 3

Binding Constants for Metal Complexes of Ligand 7

|  | $Al^{3+}$ | $Cu^{2+}$ | $Ni^{2+}$ | $Zn^{2+}$ | $Mn^{2+}$ |
|---|---|---|---|---|---|
| $\beta_{110}$ | 16.07 | 13.97 | 9.02 | 9.18 | 7.15 |
| $\beta_{11-1}$ | 11.06 |  |  | 0.35 | −0.1 |

EXAMPLE 15

Using Computational Chemistry to Predict Stability Constants

First-principles electronic-structure calculations were performed to predict the Al binding affinity of several ligands of this invention. The binding energies of a series of reference hydroxamate ligands with known Al binding constants were also calculated.

For each ligand (L) the Gibbs free energy ($\Delta G_{bind}$) associated with eq (6) was calculated.

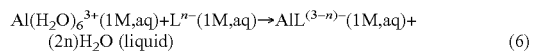

In eq (6), $L^{n-}$ refers to the fully deprotonated form of the ligand. The molecular structures studied in this project are all flexible and each has many possible conformations. In order to calculate the binding free energies, a thorough conformational search was conducted to determine the lowest-free-energy molecular conformations for all molecular species involved.

For the ligand and the Al complex, this initial step involved an automated conformational search approach (including the combined use of Genetic Algorithm, Monte Carlo simulations, and Molecular Dynamics-Simulation Annealing methods) implemented in Sybyl software (Tripos, Inc.). This provided a thorough sampling of various molecular conformations and a ranking of the conformational energies from the lowest to the highest based on the empirical molecular mechanics (MM) force field.

The geometries of the 100, lowest-energy conformations determined by the relative MM energies were optimized by using the semi-empirical quantum mechanical (QM) method PM3 implemented in the Gaussian03 program (www.gaussian.com). The conformation with the lowest PM3 energy and those whose PM3 energies were close to the lowest (within a few kcal/mol) were subjected to further geometry optimizations using a more accurate, first-principles electronic structure QM method. Specifically, density functional theory (DFT), implemented in Gaussian03 program (E. Cances, B. Mennucci and J. Tomasi, J. Phys. Chem. 1997, 107: 3032-3041; J. Tomasi, B. Mennucci, and E. Cances, Theochem 1999, 464: 211-226) with Becke's three-parameter hybrid exchange functional and the Lee-Yang-Parr correlation functional (B3LYP) in combination with the 6-31+G*basis set, was used to fully optimize all of the molecular geometries selected from the PM3 calculations. The geometries optimized at the B3LYP/6-31+G*level were used to perform single-point energy calculations at the MP2 level using 6–31+G*basis set. The solvation free energies were evaluated by performing an integral equation formulation of the polarizable continuum model (IEFPCM) at the HF/6-31+G*level (E. Cances, B. Mennucci and J. Tomasi, J. Phys. Chem, 1997, 107: 3032-3041; J. Tomasi, B. Mennucci, and E. Cances, Theochem 1999, 464: 211-226).

The theoretical calculations using the IEFPCM method systematically overestimated the binding free energies of the Al complexes. However, there was an excellent linear correlation between the calculated binding energies and the experimental Al binding constants for the five reference ligands included in the calculations, which is described by eq 7

$$\text{Log } \beta_{110} = -0.257 \, (\Delta G_{bind}) - 2.07 \quad (7)$$

with r=0.998 and a root-mean-square deviation in log $\beta_{110}$ of 0.27. The calculated binding energies and equation 7 have been used to predict the log $\beta_{110}$ values for $Al^{3+}$ binding to several new ligands. The results are shown in Table 4,

TABLE 4

Al$^{3+}$ Binding Constants from Computational Modeling

| Ligand No. | $\Delta G_{binding}$ (kcals mole$^{-1}$) | Log $\beta_{110}$ Calcd from eq 7 |
|---|---|---|
| 8 | −80.03 | 18.46 |
| 1 | −86.29 | 20.06 |
| 2 | −87.32 | 20.33 |
| 3 | −87.29 | 20.32 |
| 9 | −89.40 | 20.86 |
| 4 | −89.44 | 20.87 |

The experimental value for log $\beta_{110}$ for Ligand 1 is 21.4, which indicates that the computational modeling is underestimating the binding constants for tripodal ligands. Nevertheless, the computational results indicate that the structural modifications associated with Ligands 2, 3, 4, and 9, which elongate the sidearms of the ligand, will increase the Al binding constants by a factor of 2 to 4 compared to Ligand 1.

EXAMPLE 16

Linear Free Energy Predictions for Amide Ligands

This invention includes tripodal ligands that have amide functional groups in the ligand sidearms. Previous studies on similar ligands have reported that these amide groups, even though not directly involved in metal binding, form intramolecular hydrogen bonds that stabilize the ferric complexes (K. Matsumoto, T. Ozawa, K. Jitsukawa, H, Einaga, and H, Madsuda, Inorg. Chem. 2001, 40: 190-191; K. Matsumoto, T. Ozawa, K, Jitsukawa, H. Einaga, and H, Masuda, Chem. Commun, 2001, 978-979). Binding constants for Fe$^{3+}$ with tripodal trihydroxamate ligands are in the range of 10$^{28}$ to 10$^{33}$ (Matsumoto et al. Inorg. Chem. 2001, 40: 190-191; K. Matsumoto, N. Suzuki, T. Ozawa, K, Jitsukawa, and H. Masuda, Eur. J. Inorg. Chem. 2001, 2481-2484; C. Y. Ng, S. J. Rodgers and K. N. Raymond, Inorg. Chem. 1989, 28: 2062-2066; R. J. Motekaitis, Y. Sun, and A. E, Martell, Inorg. Chem. 1991, 30: 1554-1556), but no data on the binding of Al$^{3+}$ has been reported.

Linear free energy relationships have shown that for most chelating agents, the value for log β (Al$^{3+}$) is typically ~0.75× log β (Fe$^{3+}$) (W. R. Harris and J. Sheldon, Inorg. Chem. 1990, 29: 119-124). Such a LFER based strictly on hydroxamate ligands is shown in FIG. 1. The data in FIG. 1 are described by eq 8.

$$\text{Log } K_{Al} = 0.806(\text{Log } K_{Fe}) - 0.76 \quad (8)$$

Based on Eq (8) and Fe$^{3+}$ binding constants reported in the literature for tripodal trihydroxamic acids with amide-containing sidearms, the Al$^{3+}$ binding constants for the amide ligands included in this Invention are predicted to fall in the range of 10$^{22}$ to 10$^{26}$.

EXAMPLE 17

Binding of Al to Resin 1

The compounds and compositions of the present invention are useful in a method of removing a trivalent metal ion such as Al$^{3+}$ from an aqueous solution. This is performed by treating the aqueous solution with an effective amount of the compound or composition of the present invention. In the most preferred embodiment, the invention consists of a resin to which the chelating agent is attached by a covalent bond to form a chelating resin.

In one method of use, the resin is stirred in a solution. After the metal ions from the solution bind to the resin, the metal-depleted solution and the metal-laden resin are separated by filtration or decantation.

In a second method of use, the resin is packed in a column, and the metal-containing solution is passed through the column. The metal ions are retained on the column, while the metal-depleted solution exits from the bottom of the column.

In one possible application, the invention would be used to reduce the amount of Al$^{3+}$ contained in total parenteral nutrition solutions, particularly for TPN solutions given to neonates. The binding constants shown in Tables 1 and 2 indicate that treatment of the final TPN solution with the invention is likely to remove essential metal ions such as Fe$^{3+}$, Cu$^{2+}$ and Zn$^{2+}$ in addition to Al$^{3+}$. Thus the strongly preferred process is to use the invention to remove the Al$^{3+}$ from small volume, parenteral (SVP) solutions that are used in the preparation of TPN solutions.

The primary "culprit" SVP solutions, which are contaminated with aluminum thereby contributing aluminum to the final TPN admixture and therefore to the patient, are calcium gluconate and sodium phosphate (Driscoll, M. and D. F. Driscoll, Am. J. Health-Syst. Pharm. 2005, 62: 312-315). It should be appreciated that removal of Al$^{3+}$ from these solutions is difficult because the anions of these salts, gluconate and phosphate, respectively, are themselves strong Al-binding agents (R. J. Motekaitis and A. E. Martell, Inorg. Chem. 1984, 23: 18-23; K. Atkari, T. Kiss, R. Bertani, and R. B. Martin, Inorg. Chem. 1996, 35: 7089-7094). Thus the invention must compete against high concentrations of these anions in order to remove Al$^{3+}$ from the solution.

The compositions of the present invention are loaded into a flow-through filter device. As the SVP solution flows through the device, the aluminum is extracted from the solution. The device is provided in-line between the container of the SVP culprit solution and the TPN bag being prepared by the automated TPN compounder. The device is on the outlet side a membrane filter with a pore size small enough to sterilize the solution by filtration, retain the resin in the device and block release of large particles from the device. A screen on the inlet side contains the resin. Leur lock or similar connectors on the inlet and outlet sides enables easy connection to standard i.v. fluid administration sets.

In another medical application, the compounds and compositions of the present invention are utilized to ensure that aluminum is not inadvertently included in the dialysis solution used in peritoneal dialysis or hemodialysis. Another example is home peritoneal dialysis, where tap water is used to prepare the dialysate. If the tap water contains significant aluminum, which might have been introduced during the water treatment process, or might enter in the raw water, and which is not adequately removed during the water treatment process, the aluminum could enter the patient. In addition the compounds and compositions of the present invention could be used on a bulk scale in industry to remove aluminum from solutions such as the solutions that go into SVP containers or any material or process that is contaminated with aluminum, such as the guanine nucleotide-binding regulatory component (G/F) of adenylate cyclase, with which aluminum binds to activate adenylate cyclase. The following experimental data support the utility of the claimed compounds and compositions.

Figure 2:
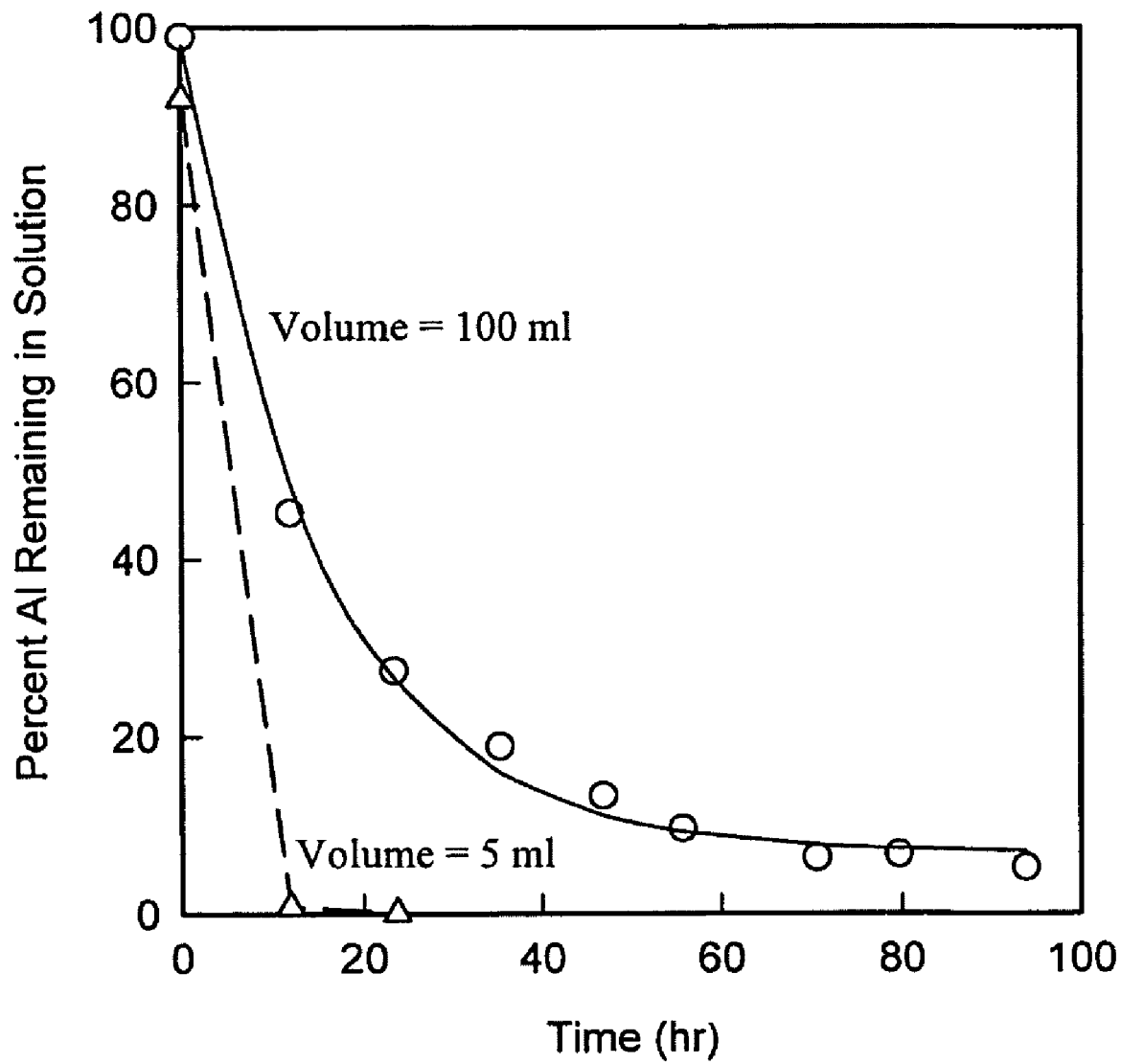
FIG. 2 is a graph demonstrating the binding of $Al^{3+}$ to 50 mg Resin 1 in which the concentration of free $Al^{3+}$ remaining in solution after the addition of 50 mcg Al at time 0 to either 100 ml or 5 ml of 4-morpholineethanesulfonic acid (MES) buffer at pH 5 has been determined by electrothermal atomic absorption spectroscopy (ETAAS).

To demonstrate the ability of Resin 1 to bind Al, 50 mg of the resin was suspended in 100 ml of a buffered (0.05 M 4-morpholineethanesulfonic acid) aqueous solution at pH 5, and 25 mcg Al was added, as an acidic solution of aluminum chloride. The free Al$^{3+}$ concentration in the sample solution was measured as a function of time by ETAAS. The results are shown in FIG. 2. The 50 mg of resin removed 94% of the $Al^{3+}$ from the solution after 94 hours and 99.2% of the $Al^{3+}$ from the solution after 287 hours (see FIG. 2 and Table 5). The removal of the $Al^{3+}$ followed first order kinetics, with a half-life of 10.5 hrs.

The $Al^{3+}$ removal experiment was repeated by adding 25 mcg of $Al^{3+}$ and 50 mg of Resin 1 to a smaller volume of only 5 ml of MES buffer at pH 5. The results are shown in FIG. 2. Under these conditions, 98% of the $Al^{3+}$ was removed from the solution within 12 hr and 99.9% after 24 hours.

Figure 3:
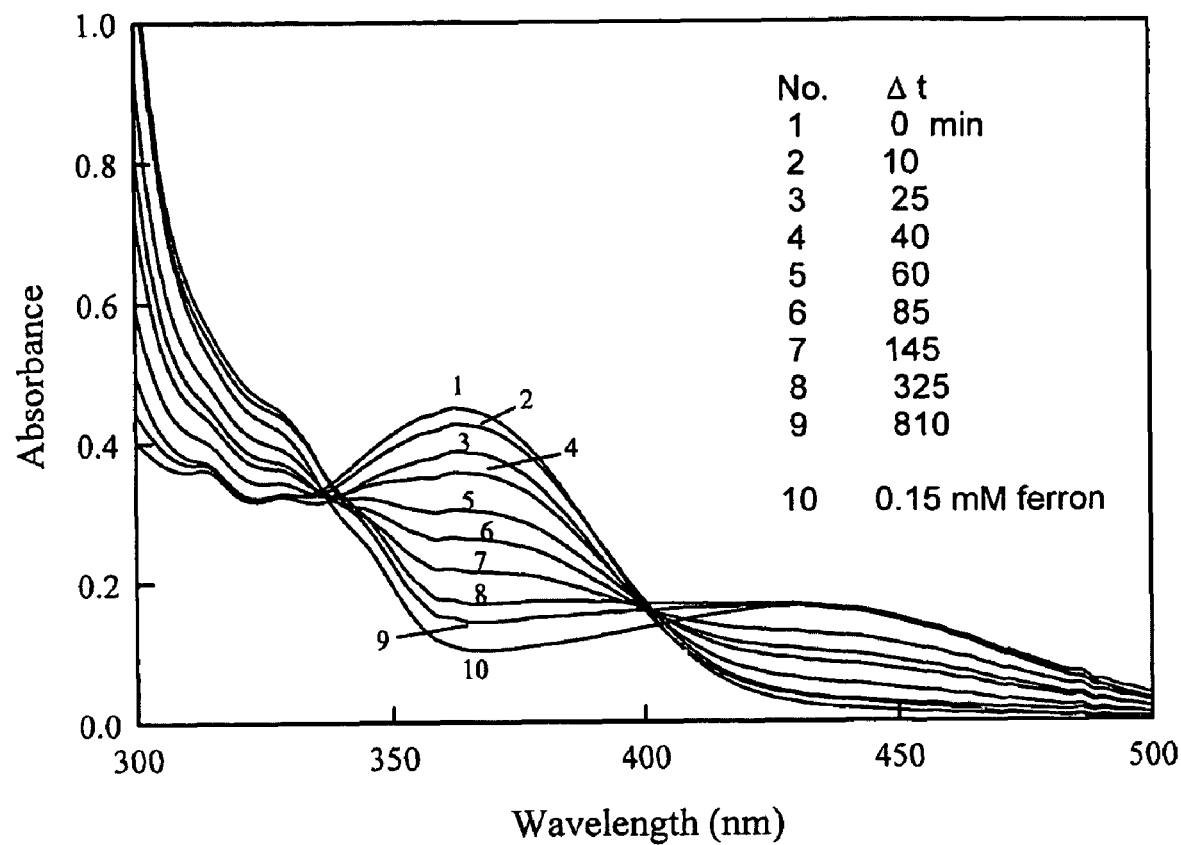
FIG. 3 is a spectrophotometry assay showing the binding of $Al^{3+}$ to Resin 1 following addition of 22.8 mg of Resin 1 to 3 ml of 0.15 mM Al-ferron at pH 5. Spectra show the decrease in the absorbance of Al-ferron at 364 nm and the increase in the absorbance of free ferron at 434 nm. Spectrum 10 shows the reference spectrum for 0.15 mM ferron.

The removal of $Al^{3+}$ from MES buffer was also followed by a spectrophotometric assay in which the weaker chelating agent 7-iodo-8-hydroxyquinoline-5-sulfonic acid (ferron) was used as an indicator for free $Al^{3+}$. The data are shown in FIG. 3. The starting solution contains a 1:1 ratio of 150 microMolar $Al^{3+}$ and ferron in a total volume of 3.0 ml, and the initial spectrum shows the peak at 360 nm indicative of the Al-ferron complex. A total of 25 mg of Resin 1 was added to the solution, and the removal of $Al^{3+}$ from the solution was monitored by the loss of the absorbance of the Al-ferron complex at 360 nm and the corresponding increase in the absorbance of free ferron at 440 nm. Based on a comparison to the final absorbance to that of a standard solution of free ferron, it is estimated that the resin removed approximately 80% of the $Al^{3+}$. The rate of Al removal corresponds to a half-life of approximately 90 min. The smaller percentage of Al removed reflected the competition for $Al^{3+}$ from the ferron. These data were used to estimate ah equilibrium constant for the binding of $Al^{3+}$ to the Resin 1 as described below.

Figure 4:
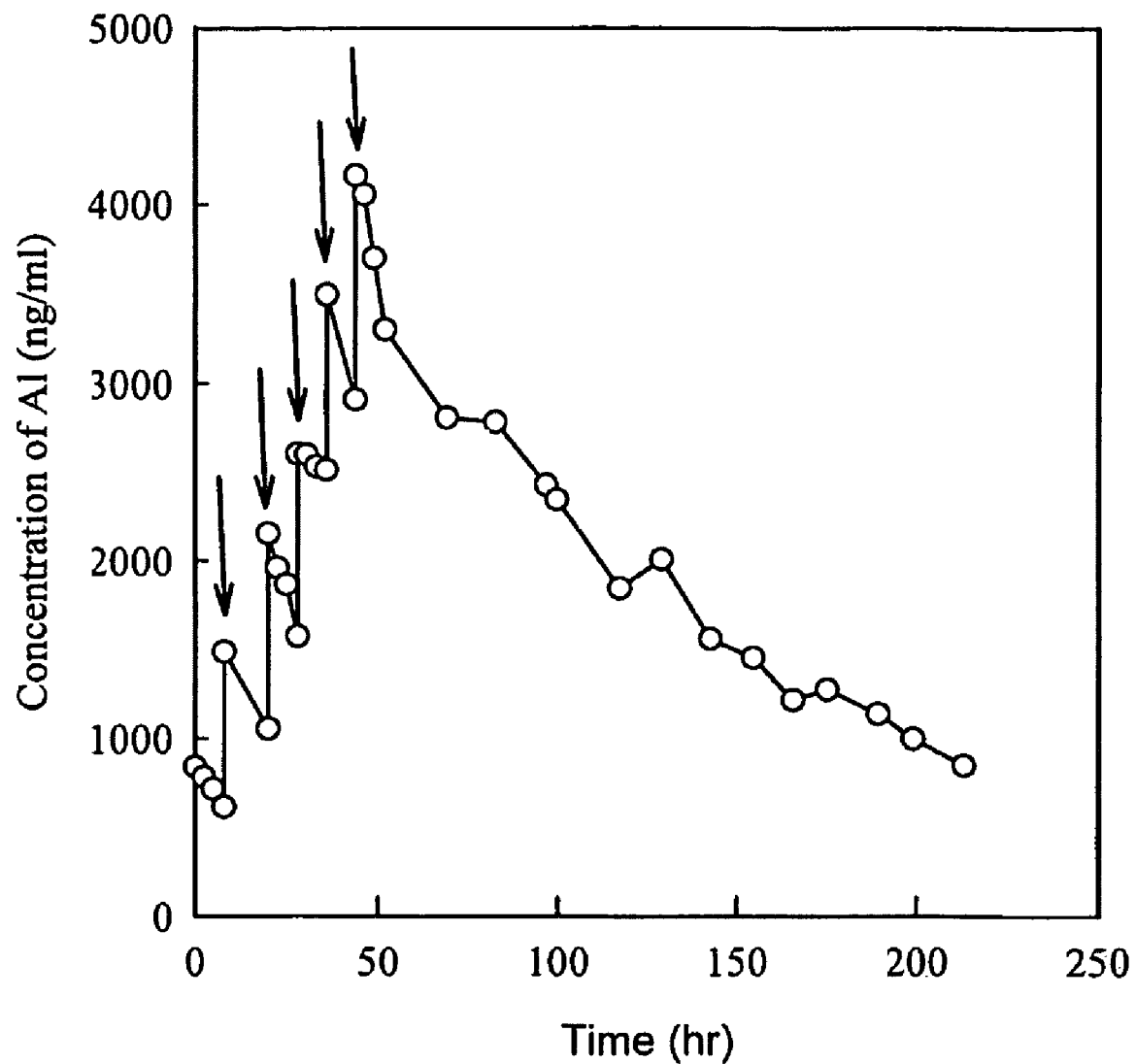
FIG. 4 is a graph illustrating the binding of $Al^{3+}$ to Resin 1 following the sequential addition of six aliquots of 100 mcg of Al to 50 mg of Resin 1 suspended in 100 ml of pH 5 MES buffer. The first aliquot of Al was added at time=0. Five subsequent additions were made at 12 hr intervals at the time indicated by the arrows on the graph. The free Al concentration was determined by ETAAS.

To determine the capacity of Resin 1 to bind Al, sequential aliquots of 100 mcg of $Al^{3+}$ were added at 8 hr intervals to 50 mg of the resin suspended in 100 ml of MES buffer at pH 5. The total amount of Al added to the solution was 6,000 ng/ml. The concentration of free Al remaining in the solution was followed by ETAAS. The results are shown in FIG. 4. Because of the slow rate of Al removal in dilute solutions, the concentration of $Al^{3+}$ accumulates to a total of approximately 4,000 ng/ml after the addition of the final aliquot of $Al^{3+}$. However, after 200 hrs the resin removed about 85% of the added $Al^{3+}$, reducing the free Al concentration to about 1,000 ng/ml. This indicates that the binding capacity of Resin 1 is at least 10,000 mcg $Al^{3+}$ per gram of resin.

The binding affinity of Resin 1 has been evaluated from four different types of experiments and the results are summarized in Table 5. Binding constants for the immobilized ligand were calculated using the speciation program HySS. A multicomponent equilibrium model was constructed for each reaction solution, in which the binding constant of Resin 1 was the only unknown binding constant. This constant was then adjusted manually until the HySS speciation model results matched the experimentally determined value for the percentage of Al bound to the resin. In all the calculations of the binding constants for the resin, the protonation constants for the immobilized ligand are assumed to be the same as those of the free ligand so that the resulting equilibrium constant can be expressed as a value of log $\beta_{110}$, rather than a pH-dependent effective binding constant.

The binding affinity of Resin 1 was determined from the final Al concentrations shown in FIG. 2 for the removal of $Al^{3+}$ from MES buffer. In these calculations, the only competitive binding agent was hydroxide ion. The calculations used hydrolysis constants for the $Al^{3+}$ for 0.1 M ionic strength taken from Mesmer and Baes (The Hydrolysis of Cation, Wiley, New York, 1976). The values of $\beta_{110}$ for the immobilized ligand of Resin 1 are listed in Table 5.

The aluminum binding constant for Resin 1 has been calculated from the spectrophotometric data shown in FIG. 3. In addition to $Al^{3+}$ hydrolysis constants, these calculations included the Al binding constants of ferron from Martell and Smith (Critical Stability Constants, Vol 3, Plenum, New York, 1979). The binding constant for Resin 1 is listed in Table 5.

The Al binding constant for Resin 1 has been determined by competition against the well-known hexadentate chelating agent 1,10-diaza-4,7-dioxadecane-1,1,10,10-tetraacetic acid (EGTA). A known amount of Resin 1 was allowed to equilibrate in a pH 6 solution containing both EGTA and $Al^{3+}$. After equilibration, the concentration of Al bound in the solution to EGTA was determined by ETAAS. Protonation constants and the Al-binding constant for EGTA were taken from Martell and Smith (Critical Stability Constants, vol 1, Plenum, New York, 1974). The binding constant for Resin 1 is listed in Table 5.

Aluminum binding constants for the Resin 1 were also measured by competition against gluconic acid. A 50 mg aliquot of the resin was added to 1 ml of a commercial solution of 0.23 M Ca(gluconate)$_2$. Analysis by ETAAS showed that the untreated solution contained 115 mcMolar $Al^{3+}$ as a contaminant. No other Al was added to the solution. Resin 1 removed approximately 10% of the Al from this solution. Based on the known binding constants for Al-gluconate, HySS was used to calculate the binding constant for the immobilized ligand on Resin 1. The binding constant for Resin 1 is listed in Table 5.

Competition experiments versus gluconate were repeated using samples in which the Commercial Ca(gluconate)$_2$ solution was diluted with pH 5 MES buffer. These solutions contained gluconate concentrations of 0.215 M, 0.1 M, and 0.046 M gluconic acid. The results are listed in Table 5.

Figure 5:
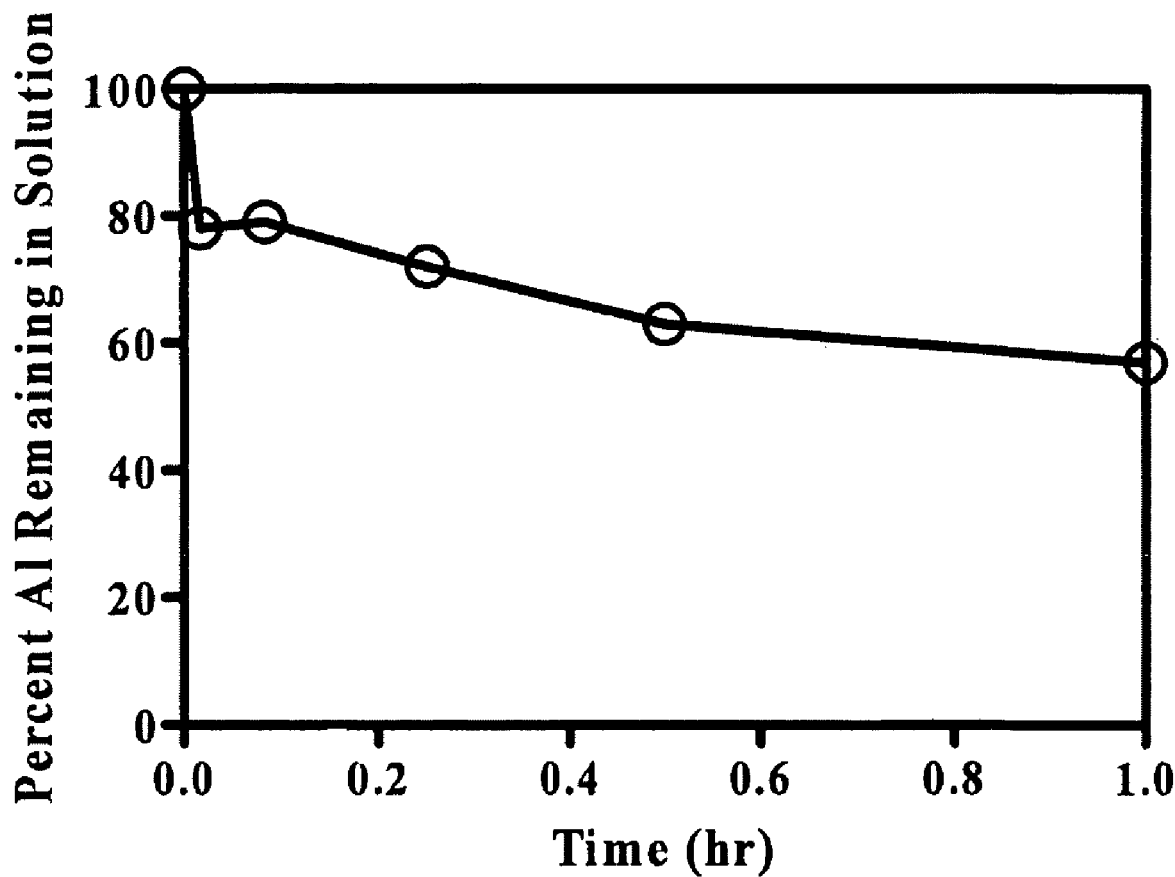
FIG. 5 is a graph illustrating the binding of $Al^{3+}$ to Resin 1 following the addition of 250 mg of Resin 1 to 0.5 ml of 0.23M calcium gluconate containing ~9000 ng Al/ml. The free Al concentration was determined by ETAAS.

To determine the ability of Resin 1 to bind Al at ratios of mg resin per ml of Ca(glutonate) that more closely model conditions one expects in a filtration device, another competition experiment versus glutonate was conducted using samples in which 250 mg of Resin 1 was added to 0.50 ml of the commercial Ca(glutonate)$_2$ solution. The initial Al concentration 9130 ng/ml. The concentration of free Al remaining in the solution was followed by ETAAS. The results are shown in FIG. 5.

TABLE 5

Summary of Experiments to Calculate the Al binding constant ($\beta_{110}$) for Resin 1

| Solution | Total Volume (ml) | pH | mg resin | Total Al (microMolar) | % Al removed | Log $\beta_{110}$ |
|---|---|---|---|---|---|---|
| 0.1M MES | 100 | 5.0 | 50 | 9.26 | 97.4 | 18.9 |
| 0.1M MES | 5 | 5.0 | 50 | 185 | 99.2 | 18.2 |
| 0.15 mM ferron | 3 | 5 | 25 | 150 | 78 | 19.2 |
| 10 mM EGTA | 1 | 5.7 | 50 | 14.9 | 58 | 18.8 |

TABLE 5-continued

Summary of Experiments to Calculate the Al binding constant ($\beta_{110}$) for Resin 1

| Solution | Total Volume (ml) | pH | mg resin | Total Al (microMolar) | % Al removed | Log $\beta_{110}$ |
|---|---|---|---|---|---|---|
| 0.23M Ca(glu)$_2$ | 1 | 5.3 | 50 | 115 | 10 | 18.5 |
| 0.108M Ca(glu)$_2$ | 1 | 5.2 | 50 | 53.8 | 18 | 18.5 |
| 0.05M Ca(glu)$_2$ | 1 | 5.2 | 50 | 25.0 | 44 | 18.7 |
| 0.023M Ca(glu)$_2$ | 1 | 5.3 | 50 | 11.5 | 72 | 18.9 |
| 0.23M Ca(glu)$_2$ | 0.5 | 4.3 | 250 | 338 | 40 | 19.0 |

The overall average binding constant for the immobilized ligand of Resin 1 from the data in Table 5 is log $\beta_{110}$=18.7±0.3. This value is about 2.7 log units less than the binding constant for free Ligand 1. Unfavorable steric interactions with the resin may be a factor, particularly when large, bulky ligands are bonded to the resin (M. Feng, L. van der Does, and A. Bantjes, J. Appl. Polymer Sci., 1995, 56: 1231-1237). The invention includes resins with longer groups linking the ligand to the polymer. It is anticipated this elongation of the linker will result in better agreement between the binding constants of the free and immobilized ligands.

It is significant that the binding constants calculated from competition with the gluconate solutions are in good agreement with the other values in Table 5. This confirms that the presence of high concentrations of $Ca^{2+}$ in the gluconate solutions has essentially no impact on the ability of the resin to remove Al from gluconate solutions.

The invention has been described herein with reference to certain preferred embodiments. However, as obvious variations will become apparent to those skilled in the art, the invention is not to be considered as limited thereto.

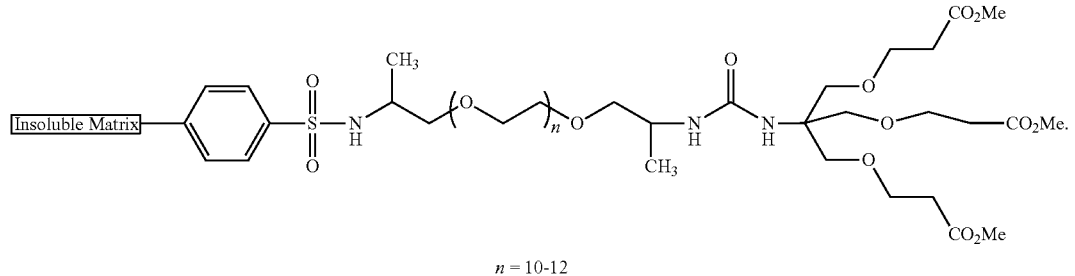
$n = 10\text{-}12$
8. Compounds having the formula:
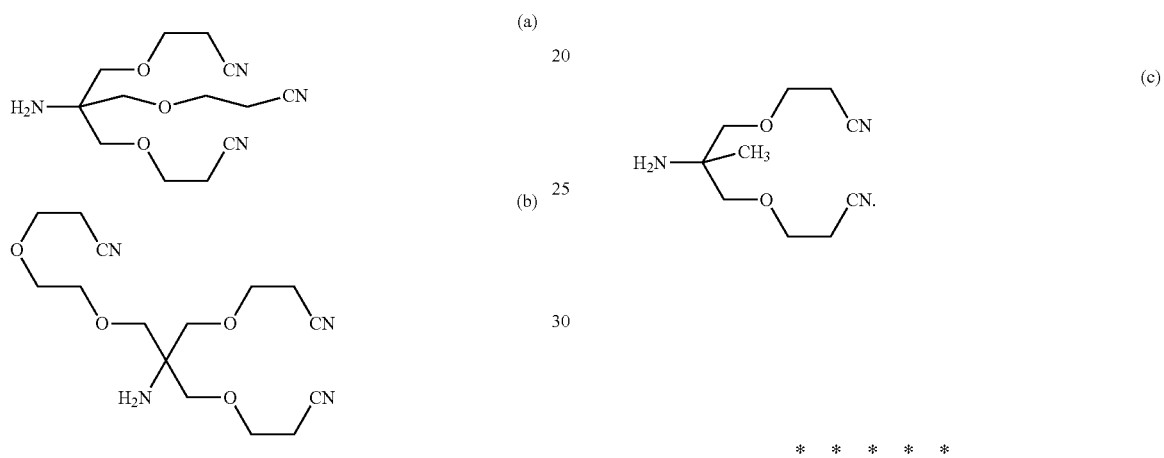

We claim:

1. A tripodal trihydroxamate chelating agent having a tris(hydroxyalkyl) aminomethane platform.

2. The chelating agent of claim 1 bonded to a polymeric resin.

3. The chelating agent of claim 2 having an $Al^{3+}$ binding constant greater than $10^{18}$.

4. The chelating agent of claim 1 having an $Al^{3+}$ binding constant greater than $10^{20}$.

5. A compound of the formula:

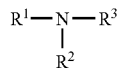

where $R^1$=hydrogen or tosylate, $R^2$=hydrogen, methyl, ethyl, n-propyl, or isopropyl, and $R^3$=

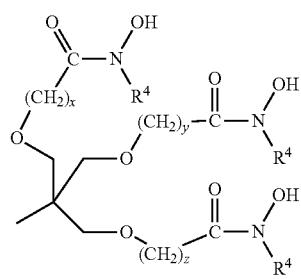

a.)

wherein x, y, and z vary independently from 2 to 4, and $R^4$=hydrogen or $C_1$-$C_{10}$ straight or branched alkyl;

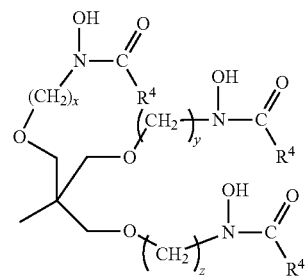

b.)

wherein x, y, and z vary independently from 2 to 4 and $R^4$=hydrogen or $C_1$-$C_{10}$ straight or branched alkyl;

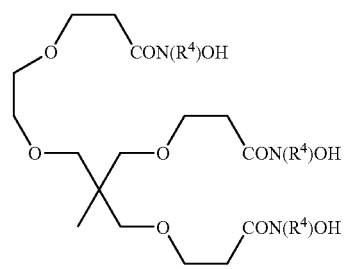

c.)

wherein $R^4$=hydrogen or $C_1$-$C_{10}$ straight or branched alkyl;

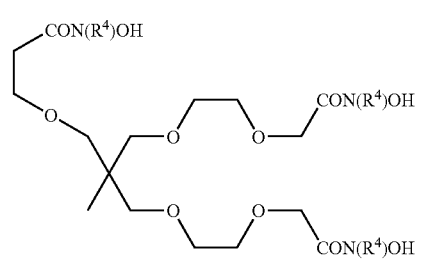

d.)

wherein $R^4$=hydrogen or $C_1$-$C_{10}$ straight or branched alkyl;

e.) 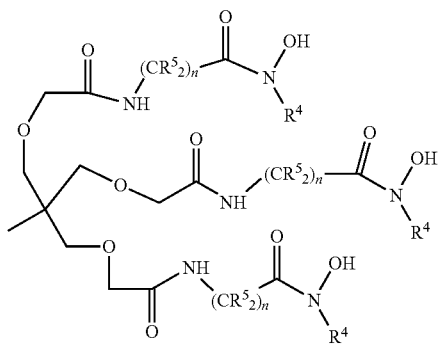

wherein n=2 or 3 and $R^5$=hydrogen or methyl, and $R^4$=hydrogen or $C_1$-$C_{10}$ straight or branched alkyl;

f.) 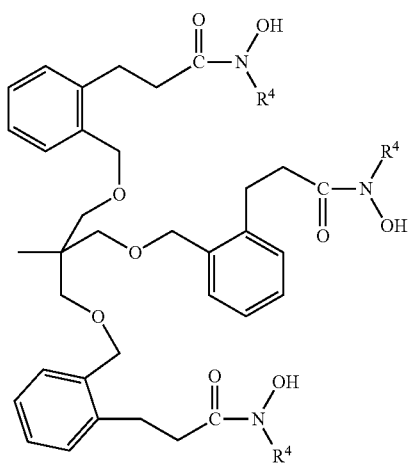

wherein $R^4$=hydrogen or $C_1$-$C_{10}$ straight or branched alkyl;

g) 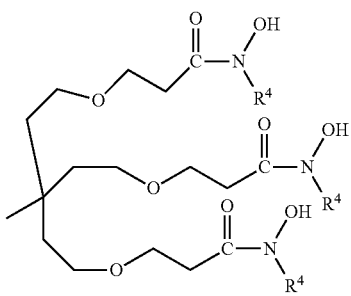

wherein $R^4$=hydrogen or $C_1$-$C_{10}$ straight or branched alkyl; and h.) 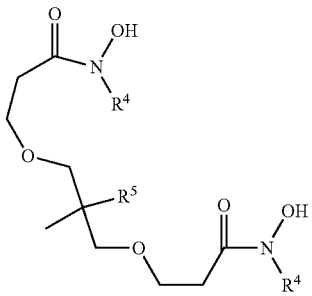

wherein $R^5$=hydrogen or methyl and $R^4$=hydrogen or $C_1$-$C_{10}$ straight or branched alkyl.

6. A compound of the formula:

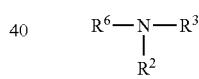

wherein $R^6$=

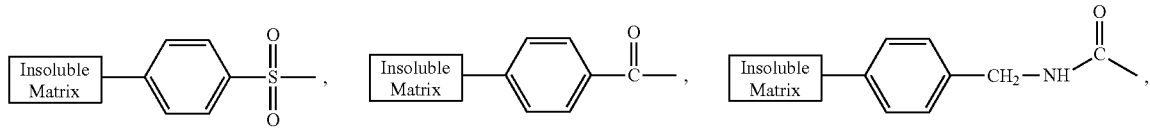

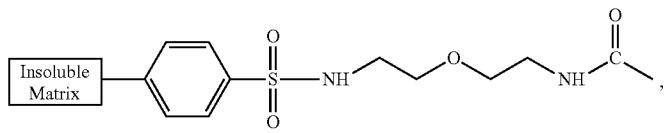

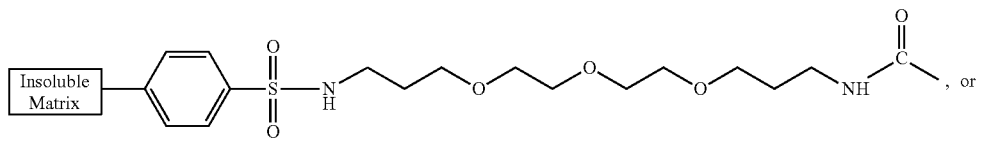

-continued

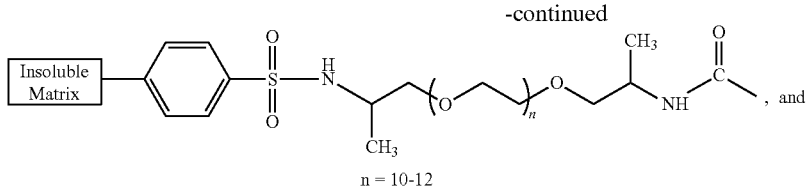

n = 10-12

$R^2$=hydrogen, methyl, ethyl; n-propyl or isopropyl and
$R^3$= a.)

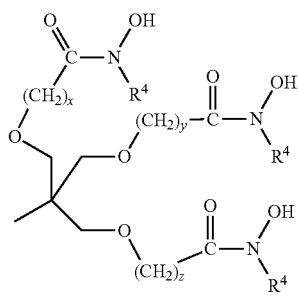

wherein x, y, and z vary independently from 2 to 4 and $R^4$=hydrogen or $C_1$-$C_{10}$ straight or branched alkyl;

b.)

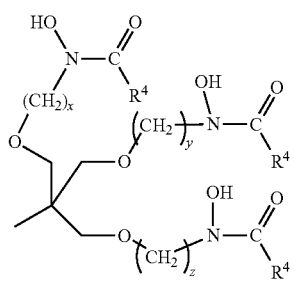

wherein x, y, and z vary independently from 2 to 4, and $R^4$=hydrogen or $C_1$-$C_{10}$ straight or branched alkyl;

c.)

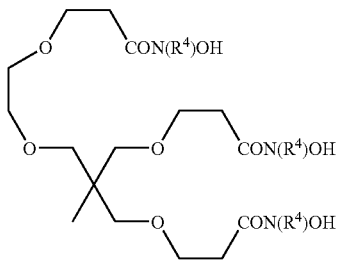

wherein $R^4$=hydrogen or $C_1$-$C_{10}$ straight or branched alkyl;

d.)

wherein $R^4$=hydrogen or $C_1$-$C_{10}$ straight or branched alkyl;

e.)

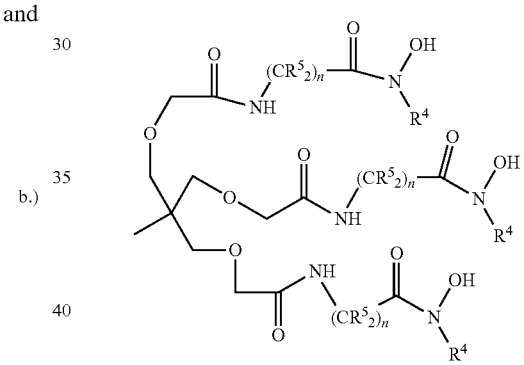

wherein n=2 or 3, $R^5$=hydrogen or methyl, and $R^4$=hydrogen or $C_1$-$C_{10}$ straight or branched alkyl;

f.)

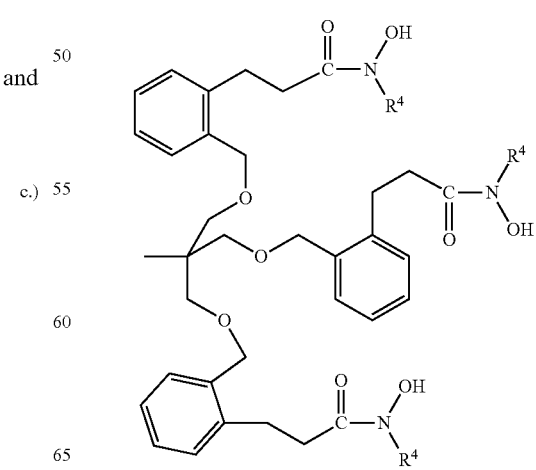

wherein R⁴=hydrogen or $C_1$-$C_{10}$ straight or branched alkyl;
wherein R⁴=hydrogen or $C_1$-$C_{10}$ straight or branched alkyl; and
g)
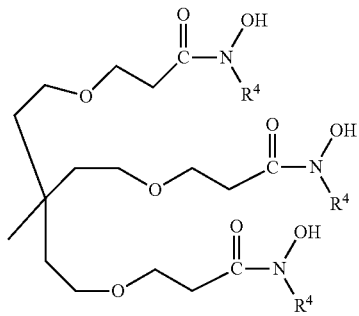
h.)
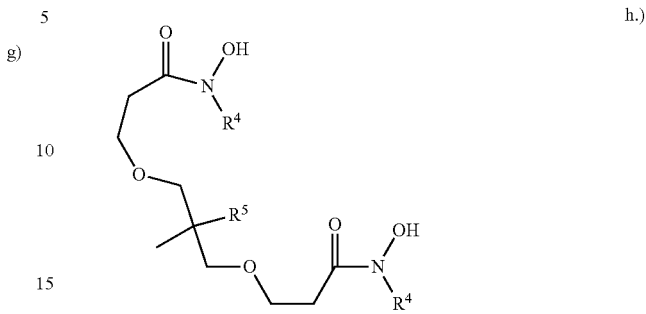
wherein R⁵=hydrogen or methyl and R⁴=hydrogen or $C_1$-$C_{10}$ straight or branched alkyl.
7. Compounds having a formula:
(a)
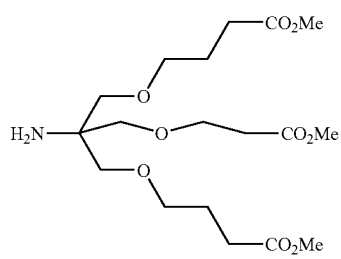
(b)
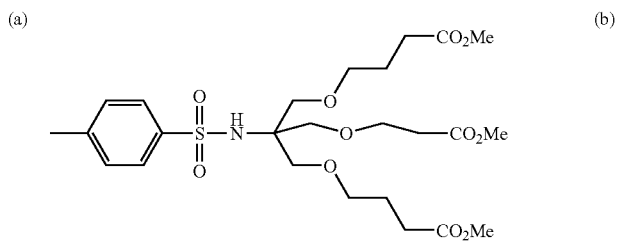
(c)
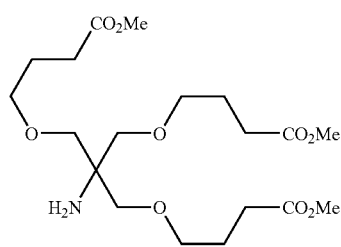
(d)
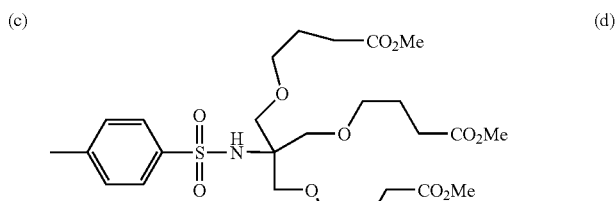
(e)
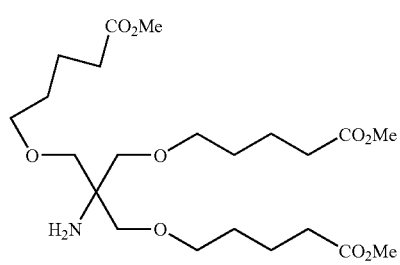
(f)
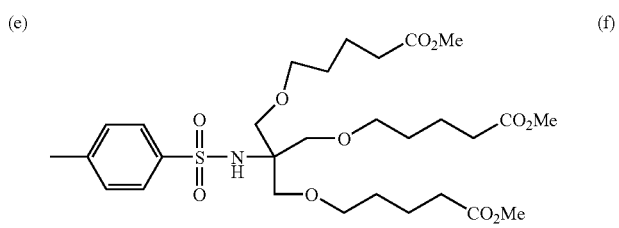
(g)
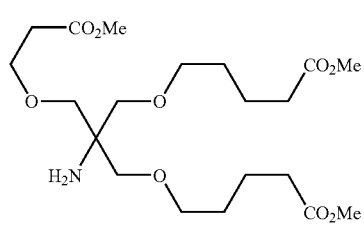
(h)
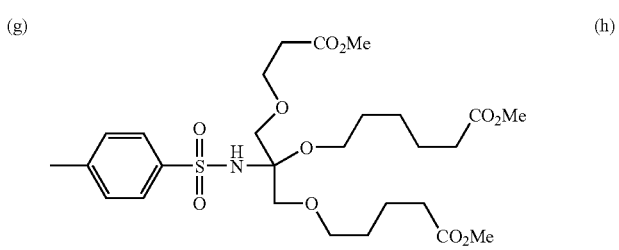

-continued
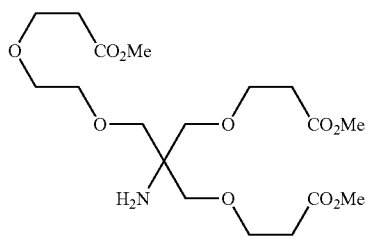 (i)
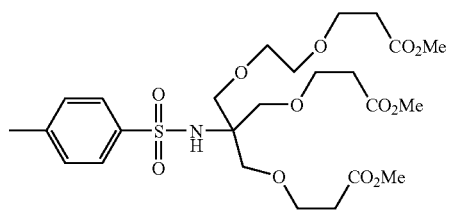 (j)
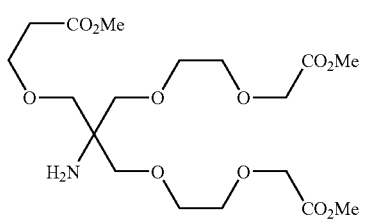 (k)
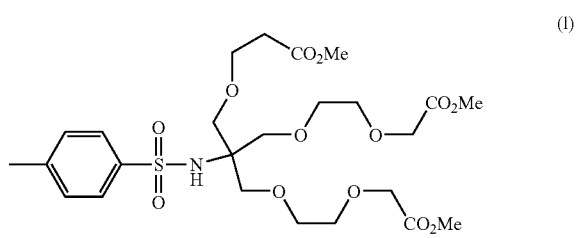 (l)
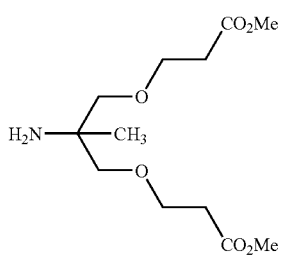 (m)
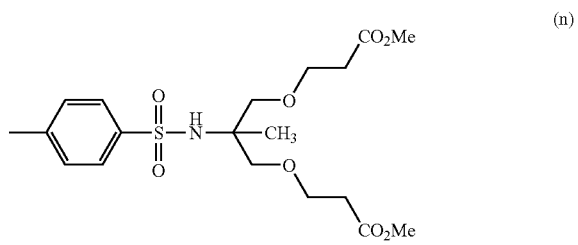 (n)
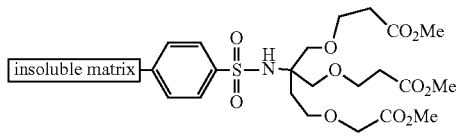 (o)
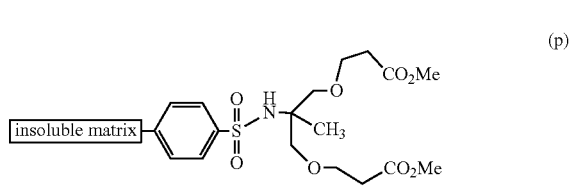 (p)
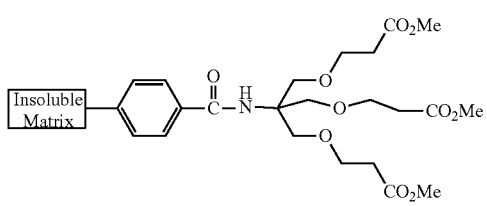 (q)
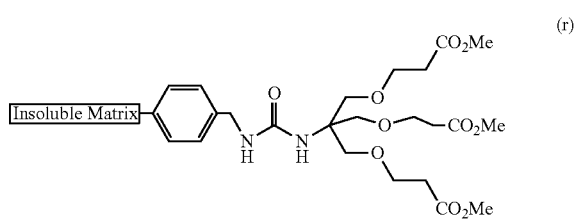 (r)
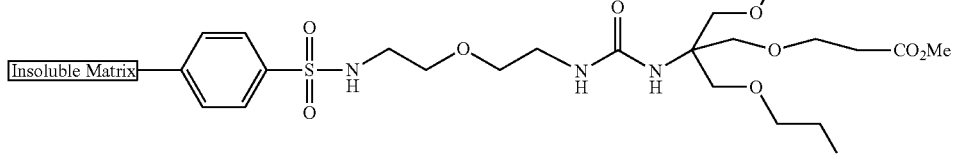 (s)
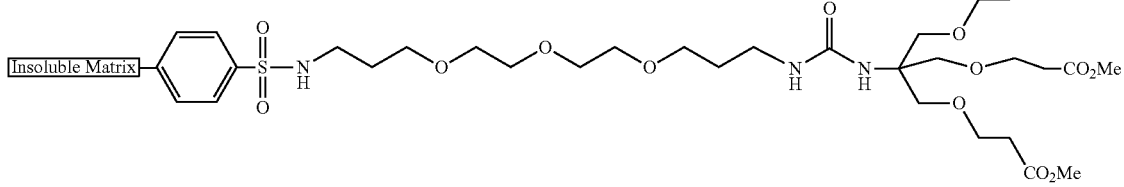 (t)